(12) United States Patent
Sakamoto et al.

(10) Patent No.: US 10,369,096 B2
(45) Date of Patent: Aug. 6, 2019

(54) POLYURETHANE POLYUREA, METHOD FOR PROVIDING SAME AND COSMETIC COMPOSITION CONTAINING SAME

(71) Applicant: ADEKA CORPORATION, Tokyo (JP)

(72) Inventors: Takao Sakamoto, Tokyo (JP); Yasuhiro Tsushima, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/528,780

(22) PCT Filed: Nov. 26, 2015

(86) PCT No.: PCT/JP2015/083210
§ 371 (c)(1),
(2) Date: May 23, 2017

(87) PCT Pub. No.: WO2016/084890
PCT Pub. Date: Jun. 2, 2016

(65) Prior Publication Data
US 2017/0319463 A1 Nov. 9, 2017

(30) Foreign Application Priority Data
Nov. 28, 2014 (JP) .................. 2014-241487

(51) Int. Cl.
| | | |
|---|---|---|
| *C08K 5/10* | (2006.01) | |
| *A61K 8/898* | (2006.01) | |
| *A61K 8/37* | (2006.01) | |
| *A61K 8/89* | (2006.01) | |
| *C08G 18/61* | (2006.01) | |
| *C08G 18/65* | (2006.01) | |
| *C08L 83/04* | (2006.01) | |
| *C08L 91/00* | (2006.01) | |
| *A61K 8/58* | (2006.01) | |
| *A61Q 19/00* | (2006.01) | |
| *C08G 18/24* | (2006.01) | |
| *C08G 18/28* | (2006.01) | |
| *C08G 18/32* | (2006.01) | |
| *C08G 18/73* | (2006.01) | |

(52) U.S. Cl.
CPC ............ *A61K 8/898* (2013.01); *A61K 8/37* (2013.01); *A61K 8/585* (2013.01); *A61K 8/89* (2013.01); *A61Q 19/00* (2013.01); *C08G 18/246* (2013.01); *C08G 18/282* (2013.01); *C08G 18/2825* (2013.01); *C08G 18/2865* (2013.01); *C08G 18/3228* (2013.01); *C08G 18/61* (2013.01); *C08G 18/65* (2013.01); *C08G 18/6529* (2013.01); *C08G 18/73* (2013.01); *C08K 5/10* (2013.01); *C08L 83/04* (2013.01); *C08L 91/00* (2013.01); *A61K 2800/10* (2013.01); *A61K 2800/48* (2013.01)

(58) Field of Classification Search
None
See application file for complete search history.

(56) References Cited

U.S. PATENT DOCUMENTS

2014/0246621 A1    9/2014 Taniguchi et al.

FOREIGN PATENT DOCUMENTS

| JP | 2000-095836 |   | 4/2000 |
|---|---|---|---|
| JP | 2000095836 | A * | 4/2000 |
| JP | 3650988 | B2 * | 5/2005 |
| JP | 2014-141087 |   | 8/2014 |
| JP | 2014141087 | A * | 8/2014 |

OTHER PUBLICATIONS

Machine Translation—Takeshi—JP2014141087A_MT (Year: 2014).*
Machine Translation—Koichiro—JP2000095836A_MT (Year: 2000).*
Machine Translation—Koichiro—JP3650988B2_MT (Year: 2005).*
Machine Translation of JP2014141087A (Year: 2014).*
Extended European Search Report dated Jun. 11, 2018 in corresponding European Patent Application No. 15862843.8.

* cited by examiner

*Primary Examiner* — Clinton A Brooks
*Assistant Examiner* — Kofi Adzamli
(74) *Attorney, Agent, or Firm* — Wenderoth, Lind & Ponack, L.L.P.

(57) ABSTRACT

A polyurethane polyurea having strong thickening and gelling effects, obtained by reacting a polyurethane polyurea prepolymer obtained from a silicone derivative starting material having a specific structure, a specific diisocyanate compound starting material and a starting material made up of a compound represented by General Formula (C) (each of which is set forth in the Description), with either or both of a nitrogen compound having a specific structure and a hydroxyl group-containing compound having a specific structure (each of which is set forth in the Description.

5 Claims, No Drawings

POLYURETHANE POLYUREA, METHOD FOR PROVIDING SAME AND COSMETIC COMPOSITION CONTAINING SAME

TECHNICAL FIELD

The present invention relates to a polyurethane polyurea usable as a gelling agent for oils. More particularly, it relates to a novel polyurethane polyurea that contains silicon in the molecule while also having both urethane bonds and urea bonds, and that is capable of thickening silicone oils or ester oils into gel or jelly form even with a small added amount, and to a cosmetic composition containing same.

BACKGROUND ART

Examples of oily components used in cosmetics include hydrocarbons, higher alcohols, ester oils, animal and plant oils, silicone oils, polyhydric alcohols, polyhydric alcohol ethers and alkyl glyceryl ethers. Because they have such effects as making the skin softer and smoother, protecting and moisturizing the skin, and removing excess oils from the skin, these components are used as starting materials in various products including basic skincare products such as cleansing oils, creams and beauty essences; make-up such as foundations, sunscreens, mascara, eye shadow and rouge; hair products such as shampoos, rinses, conditioners, hair dyes and styling products; and lip cosmetics such as lipstick and lip gloss.

With ordinary oily components, there are often concerns about the sticky feeling characteristic of oily components, safety and irritation to the skin, and stability when compounded in cosmetics and the like. Of these oily components, ester oils and silicone oils have relatively little sticky feeling and are known to be highly stable and non-irritating, so they are often preferred as oily components for compounding in cosmetics. However, the problem is that these are not very stable when compounded in cosmetics. There is commercial demand for techniques to further improve the stability of cosmetics containing ester oils and silicone oils, and, for example, additives have been developed for emulsifying ester oils and silicone oils used in cosmetics containing water, and for thickening or gelling ester oils and silicone oils used in cosmetics containing no water. In the latter case, however, there is room for further development.

For example, gelling agents that have been developed include a N-acylamino acid monoamide monoalkyl ester (PTL 1) that can harden and gel a wide variety of oily bases including silicone, conferring a hard, waxy consistency, and a silicone compound (PTL 2) containing a polyoxyalkylene group and an organic group having one or more terminal hydroxyl groups, and capable of gelling silicone oil and conferring a relatively soft, pasty consistency. However, since these gelling agents can only confer a specified waxy or pasty consistency or properties, their range of use is limited for cosmetic applications. Polyurethane compounds (PTL 3, 4) and the like have therefore been developed that confer a gel-like or jelly-like consistency that is applicable to a wide range of cosmetic applications and is more elastic, more pleasant to the touch and easier to spread on the skin, but these additives are added to cosmetics in extremely large quantities, and the thickening and gelling effects are unsatisfactory. Thickening and gelling of silicone and ester oily components is a widely marketable technology because it can lead to cosmetic diversification or in other words the development of various forms of oil-based products, and should be of interest in the cosmetic industry. There is therefore market demand for the development of thickeners and gelling agents with greater oil thickening effects, and the development of additives that can achieve thickening and gelling effects with the smallest possible added amounts.

CITATION LIST

Patent Literature

[PTL 1] WO 2007/078013
[PTL 2] Japanese Patent Application Publication No. 2007-254538
[PTL 3] Japanese Patent Application Publication No. 2011-102256
[PTL 4] Japanese Patent Application Publication No. 2011-225729

SUMMARY OF INVENTION

Technical Problem

Therefore, the problem that the present invention attempts to solve is how to provide an additive having strong thickening and gelling effects, the additive being capable of thickening and gelling silicone oils and ester oils even when added in a small amount.

Solution to Problem

As a result of earnest research, the inventors arrived at the present invention after discovering a novel polymer capable of forming a silicone oil composition or ester oil composition with a gel-like or jelly-like consistency even when added in a small amount. This is a polyurethane polyurea obtained by reacting a polyurethane polyurea prepolymer obtained from a silicone derivative starting material made up of one or two or more compounds represented by General Formula (A) below, a diisocyanate compound starting material made up of one or two or more compounds represented by General Formula (B) below and a starting material made up of one or two or more compounds represented by General Formula (C) below, with either or both of a nitrogen compound made up of one or two or more compounds represented by General Formula (D) below and a hydroxyl group-containing compound made up of one or two or more compounds represented by General Formula (E) below.

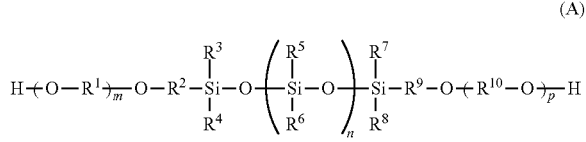

(A)

where $R^1$ and $R^{10}$ represent $C_{1-4}$ divalent hydrocarbon groups, $R^2$ and $R^9$ represent $C_{1-10}$ divalent hydrocarbon groups, each of $R^3$ to $R^8$ independently represents a $C_{1-10}$ hydrocarbon group or a group represented by General Formula (a-1), each of m and p independently represent a number from 0 to 10, and the average value of n represents a number from 0 to 2,000.

(a-1)

where $R^{11}$ represents a $C_{1-10}$ divalent hydrocarbon group, $R^{12}$ represents a $C_{1-4}$ divalent hydrocarbon group, and q represents a number from 0 to 10.

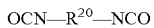  (B)

where $R^{20}$ represents a $C_{1-20}$ divalent hydrocarbon group.

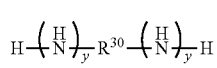  (C)

where $R^{30}$ represents a $C_{1-10}$ divalent hydrocarbon group or an oxygen atom, and y represents a number 0 or 1; however, when $R^{30}$ is a $C_{1-10}$ divalent hydrocarbon group, y represents the number 1, and when $R^{30}$ is an oxygen atom, y represents the number 0.)

  (D)

where each of $R^{40}$ and $R^{41}$ independently represent a hydrogen atom or a $C_{1-30}$ hydrocarbon group optionally having one or two or more substituents selected from a nitro group, an ether group, a carbonyl group, an ester group and an amide group. However, $R^{40}$ and $R^{41}$ may not both be hydrogen atoms.

  (E)

where $R^{50}$ represents a $C_{1-30}$ hydrocarbon group optionally having one or two or more substituents selected from a nitro group, an ether group, a carbonyl group, an ester group and an amide group.

Advantageous Effects of Invention

The polyurethane polyurea of the present invention can thoroughly thicken or gel silicone oils and ester oils when added to these in a small amount. This polyurethane polyurea may be used as a thickener or gelling agent in cosmetic compositions and the like containing silicone oils or ester oils.

DESCRIPTION OF EMBODIMENTS

The polyurethane polyurea of the present invention is a novel polymer capable of forming a silicone oil composition or ester oil composition with a gel-like or jelly-like consistency when added in a small amount. Specifically, this is a polyurethane polyurea manufactured by reacting a polyurethane polyurea prepolymer obtained from a silicone derivative starting material made up of one or two or more compounds represented by General Formula (A) below, a diisocyanate compound starting material made up of one or two or more compounds represented by General Formula (B) below and a starting material made up of one or two or more compounds represented by General Formula (C) below, with either or both of a nitrogen compound made up of one or two or more compounds represented by General Formula (D) below and a hydroxyl group-containing compound made up of one or two or more compounds represented by General Formula (E) below. In this Description, the "polyurethane polyurea prepolymer" is a precursor of the polyurethane polyurea of the present invention, and is manufactured by reacting a silicone derivative starting material made up of one or two or more compounds represented by General Formula (A), a diisocyanate compound starting material made up of one or two or more compounds represented by General Formula (B) and a starting material made up of one or two or more compounds represented by General Formula (C).

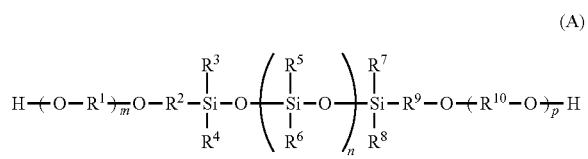  (A)

where $R^1$ and $R^{10}$ represent $C_{1-4}$ divalent hydrocarbon groups, $R^2$ and $R^9$ represent $C_{1-10}$ divalent hydrocarbon groups, each of $R^3$ to $R^8$ independently represent a $C_{1-10}$ hydrocarbon group or a group represented by General Formula (a-1), each of m and p independently represent a number from 0 to 10, and the average value of n represents a number from 0 to 2,000.

  (a-1)

where $R^{11}$ represents a $C_{1-10}$ divalent hydrocarbon group, $R^{12}$ represents a $C_{1-4}$ divalent hydrocarbon group, and q represents a number from 0 to 10.

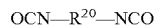  (B)

where $R^{20}$ represents a $C_{1-20}$ divalent hydrocarbon group.

  (C)

where $R^{30}$ represents a $C_{1-10}$ divalent hydrocarbon group or oxygen atom, and y represents a number 0 or 1; however, when $R^{30}$ is a $C_{1-10}$ divalent hydrocarbon group, y represents the number 1, and when $R^{30}$ is an oxygen atom, y represents the number 0.

  (D)

where each of $R^{40}$ and $R^{41}$ independently represent a hydrogen atom or a $C_{1-30}$ hydrocarbon group optionally having one or two or more substituents selected from a nitro group, an ether group, a carbonyl group, an ester group and an amide group. However, $R^{40}$ and $R^{41}$ may not both be hydrogen atoms.

  (E)

where $R^{50}$ represents a $C_{1-30}$ hydrocarbon group optionally having one or two or more substituents selected from a nitro group, an ether group, a carbonyl group, an ester group and an amide group.

One starting material of the polyurethane polyurea prepolymer is a silicone derivative represented by General Formula (A), which is explained in detail here. Each of $R^1$ and $R^{10}$ in General Formula (A) represent a $C_{1-4}$ divalent hydrocarbon group, and examples of such groups include methylene; ethylene; propane-1,3-diyl (linear propylene); branched propylene groups such as propane-1,2-diyl and propane-2,2-diyl; linear butylene groups such as butane-1,4-diyl, butane-1,2-diyl, butane-1,3-diyl, butane-2,3-diyl, butane-1,1-diyl and butane-2,2-diyl; and branched butylene groups such as 2-methylpropane-1,3-diyl and 2-methylpropane-1,2-diyl. Of these, an ethylene group, propane-1,3-diyl group, propane-1,2-diyl group or propane-2,2-diyl group is preferred for increasing the thickening and gelling effects of the polyurethane polyurea of the present invention, and an ethylene group is especially desirable. All of the $R^1$ groups may be the same group, or they may be different groups. Similarly, all the $R^{10}$ groups may be the same group, or they may be different groups.

$R^2$ and $R^9$ in General Formula (A) represent $C_{1-10}$ divalent hydrocarbon groups, and examples of such groups include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, cyclopentylene and cyclohexylene groups; and aromatic hydrocarbon groups such as phenylene, methylphenylene, ethylphenylene, propylphenylene, butylphenylene, dimethylphenylene, diethylphenylene and phenethylene groups. Of these, a divalent aliphatic hydrocarbon group is preferred for increasing the thickening and gelling effects of the polyurethane polyurea of the present invention, an ethylene, linear propylene or branched propylene group is more preferred, an ethylene or linear propylene group is still more preferred, and a linear propylene group is especially preferred.

In General Formula (A), each of m and p is independently a number from 0 to 10, and for purposes of increasing the thickening and gelling effects of the polyurethane polyurea of the present invention, m is preferably a number from 1 to 4, or more preferably 1 or 2, or most preferably 1. The average value of n represents a number from 0 to 2,000, and for purposes of increasing the thickening and gelling effects of the polyurethane polyurea of the present invention, it is preferably 10 to 1,000, or more preferably 20 to 500, or still more preferably 30 to 200, or yet more preferably 35 to 135, or most preferably 35 to 65.

In General Formula (A), each of $R^3$ to $R^8$ independently represents a $C_{1-10}$ hydrocarbon group or a group represented by General Formula (a-1), and $C_{1-10}$ hydrocarbon groups are preferred for reasons of availability. All of the $R^5$ groups in General Formula (A) may be the same, or they may be different groups. All of the $R^6$ groups in General Formula (A) may be the same, or they may be different groups. Examples of $C_{1-10}$ hydrocarbon groups include aliphatic hydrocarbon groups such as methyl, ethyl, linear propyl, branched propyl, linear butyl, branched butyl, linear pentyl, branched pentyl, linear hexyl, branched hexyl, linear heptyl, branched heptyl, linear octyl, branched octyl, linear nonyl, branched nonyl, linear decyl, branched decyl, cyclopentyl and cyclohexyl groups; and aromatic hydrocarbon groups such as phenyl, methylphenyl, ethylphenyl, propylphenyl, butylphenyl, dimethylphenyl, diethylphenyl and phenethyl groups. Of these, a methyl, ethyl, linear propyl or branched propyl group is preferred because the starting materials are easier to obtain, a methyl or ethyl group is more preferred, and a methyl group is still more preferred.

In General Formula (a-1), $R^{11}$ represents a $C_{1-10}$ divalent hydrocarbon group, and examples of such groups include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, cyclopentylene and cyclohexylene groups; and aromatic hydrocarbon groups such as phenylene, methylphenylene, ethylphenylene, propylphenylene, butylphenylene, dimethylphenylene, diethylphenylene and phenethylene groups. Of these, a divalent aliphatic hydrocarbon group is preferred for increasing the thickening and gelling effects of the polyurethane polyurea of the present invention, an ethylene, linear propylene or branched propylene group is more preferred, and an ethylene or linear propylene group is still more preferred.

In General Formula (a-1), $R^{12}$ represents a $C_{1-4}$ divalent hydrocarbon group, and examples of such groups include a methylene group; an ethylene group; a propane-1,3-diyl (linear propylene) group; branched propylene groups such as propane-1,2-diyl and propane-2,2-diyl; linear butylene groups such as butane-1,4-diyl, butane-1,2-diyl, butane-1,3-diyl, butane-2,3-diyl, butane-1,1-diyl and butane-2,2-diyl; and branched butylene groups such as 2-methylpropane-1,3-diyl and 2-methylpropane-1,2-diyl. Of these, an ethylene, propane-1,3-diyl, propane-1,2-diyl or propane-2,2-diyl group is preferred for increasing the thickening and gelling effects of the polyurethane polyurea of the present invention, and an ethylene group is especially desirable. All of the $R^{12}$ groups may be the same group, or they may be different groups.

q represents a number from 0 to 10, and q is preferably 1 to 4 or more preferably 1 or 2 in order to increase the thickening and gelling effects of the polyurethane polyurea of the present invention.

The weight-average molecular weight of the silicone derivative represented by General Formula (A) is preferably 500 to 100,000, or more preferably 2,000 to 40,000, or still more preferably 3,000 to 10,000, or yet more preferably 3,000 to 5,000 to make it easier to obtain the thickening and gelling effects of the polyurethane polyurea of the present invention. If the weight-average molecular weight is greater than 100,000 the thickening and gelling effects may be reduced, while if it is less than 500 there are cases where the thickening and gelling effects may not be obtained.

The weight-average molecular weight can be calculated from the number of hydroxyl groups in each silicone derivative and the hydroxyl value of each silicone derivative. The hydroxyl value may be a value measured by an ordinary measurement method, such as the acetylation method or phthalation method. The weight-average molecular weight may also be determined by GPC measurement and styrene conversion, and either method may be selected as necessary.

One kind of the silicone derivative represented by General Formula (A) may be used as a starting material, or two or more kinds may be used. However, the effects of the present invention are more easily obtained by using one kind of starting material.

Since the silicone derivative represented by General Formula (A) is a known substance, it can be produced by a known method and used as a starting material of the polyurethane polyurea of the present invention, or it may be purchased as a commercial product and used as a starting material.

The diisocyanate compound represented by General Formula (B), which is a starting material of the polyurethane polyurea precursor, is explained here in detail. Examples of the diisocyanate compound represented by General Formula (B) include aliphatic diisocyanates such as methylene diisocyanate, dimethylene diisocyanate, trimethylene diisocyanate, tetramethylene diisocyanate, pentamethylene diisocyanate, hexamethylene diisocyanate, heptamethylene diisocyanate, octamethylene diisocyanate, nonamethylene diisocyanate, decamethylene diisocyanate, dipropyl ether diisocyanate, 2,2-dimethylpentane diisocyanate, 3-methoxyhexane diisocyanate, octamethylene diisocyanate, 2,2,4-trimethylpentane diisocyanate, nonamethylene diisocyanate, decamethylene diisocyanate, 3-butoxyhexane diisocyanate, 1,4-butylene glycol dipropyl ether diisocyanate and thiodihexyl diisocyanate; aromatic diisocyanates such as metaphenylene diisocyanate, paraphenylene diisocyanate, 2,4-tolylene diisocyanate, 2,6-tolylene diisocyanate, dimethylbenzene diisocyanate, ethylbenzene diisocyanate, isopropylbenzene diisocyanate, tolidine diisocyanate, 1,4-naphthalene diisocyanate, 1,5-naphthalene diisocyanate, 2,6-naphthalene diisocyanate, 2,7-naphthalene diisocyanate, biphenyl diisocyanate, 3,3'-dimethylbiphenyl diisocyanate, 3,3'-dimethoxybiphenyl diisocyanate, diphenylmethane-4,4'-diisocyanate, 2,2'-dimethyldiphenylmethane-4,4'-diisocyanate, diphenyldimethylmethane-4,4'-diisocyanate, 2,5,2',5'-tetramethyldiphenylmethane-4,4'-diisocyanate, cyclohexyl bis(4-isocyanatophenyl)methane, 3,3'-dimethoxydiphenylmethane-4,4'-diisocyanate, 4,4'-dimethoxydiphenylmethane-3,3'-diisocyanate, 4,4'-diethoxydiphenylmethane-3,3'-diisocyanate, 2,2'-dimethyl-5,5'-dimethoxydiphenylmethane-4,4'-diisocyanate, 3,3'-dichlorodiphenyldimethylmethane-4,4'-diisocyanate, benzophenone-3,3'-diisocyanate, metaxylylene diisocyanate, paraxylylene diisocyanate and tetramethylxylylene diisocyanate; and alicyclic diisocyanates such as hydrogenated xylylene diisocyanate, isophorone diisocyanate and dicyclohexylmethane diisocyanate.

Of the diisocyanate compounds listed above, aliphatic diisocyanates are preferred because of their strong thickening and gelling effects on silicone oils and ester oils, methylene diisocyanate, dimethylene diisocyanate, trimethylene diisocyanate, tetramethylene diisocyanate, pentamethylene diisocyanate, hexamethylene diisocyanate, heptamethylene diisocyanate, octamethylene diisocyanate, nonamethylene diisocyanate and decamethylene diisocyanate are more preferred, and hexamethylene diisocyanate is especially preferred. Moreover, one kind of the diisocyanate compound represented by General Formula (B) may be used as a starting material, or two or more kinds may be used. However, the effects of the present invention are more easily obtained by using one kind of starting material. Thus, $R^{20}$ in General Formula (B) may be any $C_{1-20}$ hydrocarbon group, but is preferably one of the diisocyanate compounds listed above in which the two isocyanate groups are removed.

Since the diisocyanate compound represented by General Formula (B) is a known substance, it can be produced by a known method and used as a starting material of the polyurethane polyurea of the present invention, or it may be purchased as a commercial product and used as a starting material.

The compound represented by General Formula (C), which is a starting material of the polyurethane polyurea prepolymer, is explained here in detail. $R^{30}$ in General Formula (C) represents a $C_{1-10}$ divalent hydrocarbon group or an oxygen atom. Examples of $C_{1-10}$ divalent hydrocarbon groups include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, cyclopentylene and cyclohexylene groups; and aromatic hydrocarbon groups such as phenylene, methylphenylene, ethylphenylene, propylphenylene, butylphenylene, dimethylphenylene, diethylphenylene and phenethylene groups. y represents a number 0 or 1, and when $R^{30}$ is a $C_{1-10}$ divalent hydrocarbon group, y represents the number 1, and when $R^{30}$ is an oxygen atom, y represents the number 0. From the standpoint of easy procurement of the starting materials, the compound represented by General Formula (C) is preferably a compound in which $R^{30}$ is a $C_{1-6}$ divalent aliphatic hydrocarbon group or an oxygen atom, or more preferably a compound in which $R^{30}$ is an ethylene, linear butylene, linear pentylene or linear hexylene group or an oxygen atom, or still more preferably a compound in which $R^{30}$ is an ethylene group or an oxygen atom. One kind of the compound represented by General Formula (C) may be used as a starting material, or two or more kinds may be used, but the effects of the present invention are more easily obtained by using one kind of starting material.

The compound represented by General Formula (C) is a known substance, and can be purchased as a commercial product.

The nitrogen compound represented by General Formula (D) that is reacted with the polyurethane polyurea prepolymer is explained in detail here. Examples of the nitrogen compound represented by General Formula (D) include amines such as methylamine, dimethylamine, ethylamine, diethylamine, n-propylamine, di-n-propylamine, isopropylamine, diisopropylamine, n-butylamine, di-n-butylamine, branched butylamine, n-pentylamine, branched pentylamine, n-hexylamine, branched hexylamine, n-heptylamine, branched heptylamine, n-octylamine, branched octylamine, n-nonylamine, branched nonylamine, n-decylamine, branched decylamine, n-undecylamine, branched undecylamine, n-dodecylamine, branched dodecylamine, n-tridecylamine, branched tridecylamine, n-tetradecylamine, branched tetradecylamine, n-hexadecylamine, branched hexadecylamine, n-octadecylamine, branched octadecylamine, n-eicosylamine, branched eicosylamine, n-docosylamine and branched docosylamine; and anilines such as aniline, methylaniline, dimethylaniline, methoxyaniline, ethoxyaniline, methoxymethylaniline, trimethylaniline, isopropylaniline, tetramethylaniline, acetamidoaniline and aminopyridine.

Thus, although each of $R^{40}$ and $R^{41}$ in General Formula (D) may independently represent either a hydrogen atom or any $C_{1-30}$ hydrocarbon group optionally having one or two or more substituents selected from a nitro group, an ether group, a carbonyl group, an ester group and an amide group (as long as $R^{40}$ and $R^{41}$ are not both hydrogen atoms), specific groups corresponding to the nitrogen compounds listed above are preferred from the standpoint of ease of procuring the starting materials. Of the nitrogen compounds listed above, those in which either one of $R^{40}$ and $R^{41}$ is a hydrogen atom while the other is a $C_{1-20}$ hydrocarbon group are preferred for obtaining good reactivity and increasing the thickening and gelling effects of the polyurethane polyurea of the present invention, while those in which either one of $R^{40}$ and $R^{41}$ is a hydrogen atom while the other is a $C_{1-10}$ hydrocarbon group are more preferred, and those in which either one of $R^{40}$ and $R^{41}$ is a hydrogen atom while the other is a $C_{2-6}$ hydrocarbon group are still more preferred. When either one or both of $R^{40}$ and $R^{41}$ are hydrocarbon groups, the hydrocarbons preferably have no substituents because this makes the reaction easier to control. Also, one kind of the nitrogen compound represented by General Formula (D) may be used as a starting material, or two or more kinds may be used, but the effects of the present invention are more easily obtained by using one kind of starting material. The nitrogen compound represented by General Formula (D) is a known substance, and may be purchased as a commercial product.

The hydroxyl group-containing compound represented by General Formula (E), which is a starting material that is reacted with the polyurethane polyurea prepolymer, is explained next in detail. Examples of the hydroxyl group-containing compound represented by General Formula (E) include alcohols such as methanol, ethanol, n-propanol, branched propanol, n-butanol, branched butanol, t-butanol, n-pentanol, branched pentanol, neopentanol, t-pentanol, n-hexanol, branched hexanol, n-heptanol, branched heptanol, n-octanol, 2-ethylhexanol, branched octanol, n-nonanol, branched nonanol, n-decanol, branched decanol, n-undecanol, branched undecanol, n-dodecanol, branched dodecanol, n-tridecanol, branched tridecanol, n-tetradecanol, branched tetradecanol, n-hexadecanol, branched hexadecanol, n-octadecanol, branched octadecanol, n-oleyl alcohol, n-eicosanol, n-docosanol, n-tetracosanol, n-hexacosanol, n-octacosanol, n-myricyl alcohol, laccerol, n-tetratriacontanol, 2-butyloctanol, 2-butyldecanol, 2-hexyloctanol, 2-hexyldecanol, 2-octyldecanol, 2-hexyldodecanol, 2-octyldodecanol, 2-decyltetradecanol, 2-dodecylhexadecanol, 2-hexadecyloctadecanol, 2-tetradecyloctadecanol, cyclopentanol, cyclohexanol, cycloheptanol, methyl cyclopentanol, methyl cyclohexanol, methyl cycloheptanol, benzyl alcohol and benzylidene sorbitol; and phenols such as phenol, cresol, dimethylphenol, ethylphenol, n-propylphenol, t-butylphenol, n-pentylphenol, n-hexylphenol, n-heptylphenol, n-octylphenol, 2-ethylhexylphenol, n-nonylphenol, n-decylphenol, n-undecylphenol, n-dodecylphenol, phenylphenol, benzylphenol, styrenated phenol, p-cumylphenol, acetoamidophenol, p-phenoxyphenol p-hydroxybenzophenone and hydroxypyridine.

Thus, $R^{50}$ in General Formula (E) may be any $C_{1-30}$ hydrocarbon group optionally having one or two or more substituents selected from a nitro group, an ether group, a carbonyl group, an ester group and an amide group, but specifically from the standpoint of ease of procurement, it is preferably one of the hydroxyl group-containing compounds listed above in which the hydroxyl group is removed. Of the hydroxyl group-containing compounds listed above, those in which $R^{50}$ is a $C_{1-20}$ hydrocarbon group are preferred for obtaining good reactivity and increasing the thickening and gelling effects of the polyurethane polyurea of the present invention, while those in which $R^{50}$ is a $C_{1-10}$ hydrocarbon group are more preferred, and those in which $R^{50}$ is a $C_{2-8}$ hydrocarbon group are still more preferred. To facilitate control of the reaction the hydrocarbon in $R^{50}$ preferably has no substituent. Moreover, one kind of the hydroxyl group-containing compound represented by General Formula (E) may be used as a starting material, or two or more kinds may be used, but the effects of the present invention are more easily obtained by using one kind of starting material.

The hydroxyl group-containing compound represented by General Formula (E) is a known substance, and can be purchased as a commercial product.

For the nitrogen compound represented by General Formula (D) and the hydroxyl group-containing compound represented by General Formula (E), which are starting materials that are reacted with the polyurethane polyurea prepolymer, the one or two or more kinds of the nitrogen compound represented by General Formula (D) may be used alone or the one or two or more kinds of the hydroxyl group-containing compound represented by General Formula (E) may be used alone, or else the one or two or more kinds of the nitrogen compound represented by General Formula (D) may be used in combination with the one or two or more kinds of the hydroxyl group-containing compound represented by General Formula (E). To obtain the effects of the present invention more easily, preferably either the one or two or more kinds of the nitrogen compound represented by General Formula (D) are used alone or the one or two or more kinds of the hydroxyl group-containing compound represented by General Formula (E) are used alone.

The method of using the various compounds represented by General Formulae (A) to (E) above as starting materials to manufacture the polyurethane polyurea of the present invention is not particularly limited, and a known method may be used. Preferably a polyurethane polyurea prepolymer is manufactured first using the starting materials represented by General Formulae (A) to (C), after which the resulting polyurethane polyurea prepolymer is reacted with either or both of the starting materials represented by General Formula (D) and General Formula (E) to manufacture the polyurethane polyurea of the present invention. When manufacturing the polyurethane polyurea prepolymer, the individual starting materials represented by General Formulae (A) to (C) may be all mixed together at the time of the reaction and reacted, or they may be added separately and reacted. When added separately and reacted, each starting material may be divided and added to the reaction according to the progress of the reaction. After the polyurethane polyurea prepolymer has been manufactured, if one kind of compound is used for the starting materials represented by General Formulae (D) and (E), this starting material may also be divided and added to the reaction according to the progress of the reaction, and when two or more kinds of compounds are used, they may all be mixed together at the time of the reaction and reacted, or they may be added separately and reacted. When they are added separately and reacted, each starting material may be divided and added to the reaction according to the progress of the reaction.

The compounded amounts of the individual starting materials when manufacturing the polyurethane polyurea of the present invention are not particularly limited, but the following amounts are preferred. Regarding the compounded amounts of the starting materials represented by General Formulae (A) to (C) when manufacturing the polyurethane polyurea prepolymer, the diisocyanate compound represented by General Formula (B) is preferably used so that the amount of isocyanate groups in the diisocyanate compound represented by General Formula (B) is 1.1 to 3.0 moles per mole of hydroxyl groups in the silicone derivative represented by General Formula (A), in order to obtain a polyurethane polyurea with strong thickening and gelling effects on silicone oils and ester oils. In order to obtain a polyurethane polyurea with even stronger thickening and gelling effects on silicone oils and ester oils, the amount is more preferably 1.15 to 2.5 moles, or still more preferably 1.2 to 1.8 moles, or yet more preferably 1.4 to 1.6 moles. The compound represented by General Formula (C) is preferably used so that the total amount of either or both of amino groups and water (when $R^{30}$ is oxygen) in the compound represented by General Formula (C) is a total of 0.01 to 1.0 moles per mole of hydroxyl groups in the silicone derivative represented by General Formula (A), in order to obtain a polyurethane polyurea with strong thickening and gelling effects on silicone oils and ester oils. In order to obtain a polyurethane polyurea with even greater thickening and gelling effects on silicone oils and ester oils, the amount is more preferably 0.03 to 0.8 moles, or still more preferably 0.05 to 0.5 moles, or yet more preferably 0.05 to 0.2 moles.

When reacting either or both of the compounds represented by General Formula (D) and General Formula (E) with the polyurethane polyurea prepolymer, considering the yield of the polyurethane polyurea of the present invention, the compounded amounts of the compounds represented by General Formula (D) and General Formula (E) are preferably such that the total amount of either or both of the amino groups in the compound represented by General Formula (D) and the hydroxyl groups in the compound represented by General Formula (E) is 0.05 to 4.0 moles per mole of hydroxyl groups in the silicone derivative represented by General Formula (A). For the same reasons, this total amount is more preferably 0.08 to 2.0 moles, or still more preferably 0.08 to 0.5 moles.

The polyurethane polyurea of the present invention is preferably manufactured such that no highly reactive isocyanate groups are contained in the final product. Therefore, the total of the numbers of groups in the compounds represented by General Formulae (A) and (C) to (E) that react with isocyanate groups is preferably equal to or greater than the number of isocyanate groups in the diisocyanate compound represented by General Formula (B).

Next, as a specific manufacturing method, for example, the starting materials represented by General Formulae (A) to (C) are all loaded into a reaction system and collectively reacted for 1 to 5 hours at 60° C. to 100° C., after which either or both of the nitrogen compound represented by General Formula (D) and the hydroxyl group-containing compound represented by General Formula (E) is further added to the reaction system, and reacted for a further 1 to 5 hours at 60° C. to 100° C. to obtain the polyurethane polyurea of the present invention. In some cases it is even possible to obtain the polyurethane polyurea of the present invention by adding the starting materials represented by General Formulae (D) and (E) to the reaction system at the same time as the compounds represented by General Formulae (A) to (C), but it is preferable to manufacture a polyurethane polyurea prepolymer first as in the method described above because otherwise the reaction may not progress uniformly and problems may occur such as unreacted starting materials and numerous impurities in the reaction system due to differences in the reaction rates of the individual starting materials.

The polyurethane polyurea of the present invention can be manufactured using a solvent or without a solvent. However, it is desirable to use a solvent because the system as a whole may become highly viscous without a solvent, causing the reaction to become localized in the system and resulting in non-uniform reactions. Moreover, using a solvent the final product is easier to handle because it is less viscous. Using a solvent, the gelling agent of the present invention is obtained in a dissolved state in the solvent, and may be used as a product in this state, or the solvent may be removed to obtain a 100% product (pure product). Any known method may be used for removing the solvent, such as for example reduced-pressure distillation, heating and drying, spray drying, or a combination of these methods.

Examples of solvents that can be used during this reaction include hydrocarbon solvents such as hexane, cyclohexane, toluene and xylene; ester solvents such as ethyl acetate, butyl acetate, methyl branched butyl ketone branched propyl myristate and triglycerides; and various silicone oils. A solvent having no active hydrogen reactive with the isocyanate compound in the molecule is preferred because it does not adversely affect production of the polyurethane polyurea of the present invention. The amount of the solvent used is preferably 95 to 30 mass % or more preferably 85 to 50 mass % of the system as a whole. When a silicone oil or some ester oil is used as a solvent, the resulting silicone oil composition or ester oil composition may be used as is as a cosmetic.

The polyurethane polyurea of the present invention may be manufactured either with or without a catalyst. However, it is desirable to use a catalyst because this increases the reaction speed and has the effect of shortening the reaction time. Catalysts that can be used when manufacturing the polyurethane polyurea of the present invention include for example strong acids such as sulfuric acid and toluenesulfonic acid; metal halides such as titanium tetrachloride, hafnium chloride, zirconium chloride, aluminum chloride, gallium chloride, indium chloride, iron chloride, tin chloride and boron fluoride; hydroxides, alcoholates and carbonates of alkali metals and alkali earth metals, such as sodium hydroxide, potassium hydroxide, sodium methylate and sodium carbonate; metal oxides such as aluminum oxide, calcium oxide, barium oxide and sodium oxide; organic metal compounds such as tetra-branched propyl titanate, dibutyltin dichloride, dibutyltin oxide and dibutyltin bis(2-ethylhexylthioglycolate); and soaps such as sodium octylate, potassium octylate, sodium laurate and potassium laurate. The catalyst may be added to the reaction in the amount of about 0.01 to 1 mass % of the total system.

The polyurethane polyurea of the present invention may be represented by General Formula (I) below.

where G represents a group represented by General Formula (1) below, J represents a group represented by General Formula (2) below, $X^1$ represents a group represented by General Formula (3) below or a group represented by General Formula (4) below, $X^2$ represents a group represented by General Formula (5) below or a group represented by General Formula (6) below, and each of g and j represent a number from 1 to 10,000. The sequence of G and J may be either block or random, or a combination of block parts and random parts.

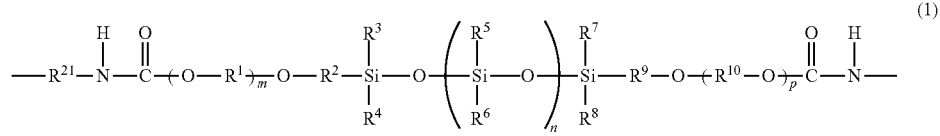

where $R^{21}$ represents a $C_{1-20}$ divalent hydrocarbon group, each of $R^1$ and $R^{10}$ independently represent a $C_{1-4}$ divalent hydrocarbon group, each of $R^2$ and $R^9$ independently represent a $C_{1-10}$ divalent hydrocarbon group, each of $R^3$ to $R^8$ independently represent a $C_{1-10}$ hydrocarbon group, a group represented by General Formula (1-1) below or a group represented by General Formula (1-2) below, each of m and p independently represent a number from 0 to 10, and the average value of n represent a number from 0 to 2,000.

(1-1)

where $R^{11}$ represents a $C_{1-10}$ divalent hydrocarbon group, $R^{12}$ represents a $C_{1-4}$ divalent hydrocarbon group, and q represents a number from 0 to 10.

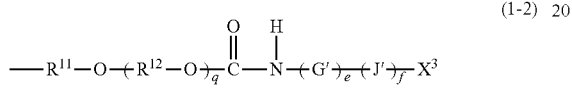
(1-2)

where $R^{11}$ represents a $C_{1-10}$ divalent hydrocarbon group, $R^{12}$ represents a $C_{1-4}$ divalent hydrocarbon group, q represents a number from 0 to 10, G' represents a group represented by General Formula (1), J' represents a group represented by General Formula (2), $X^3$ represents a group represented by General Formula (5) below or a group represented by General Formula (6) below, and each of e and f independently represent a number from 0 to 10,000. The sequence of G' and J' may be either block or random, or a combination of block parts and random parts.

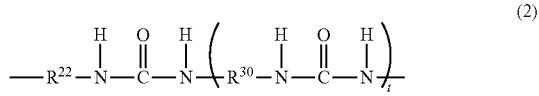
(2)

where $R^{22}$ represents a $C_{1-20}$ divalent hydrocarbon group, $R^{30}$ represents a $C_{1-10}$ divalent hydrocarbon group, and t is 0 or 1.

(3)

where each of $R^{42}$ and $R^{43}$ independently represent a hydrogen atom or a $C_{1-30}$ hydrocarbon group optionally having one or two or more substituents selected from a nitro group, an ether group, a carbonyl group, an ester group and an amide group. However, $R^{42}$ and $R^{43}$ may not both be hydrogen atoms.

(4)

where $R^{51}$ represents a $C_{1-30}$ hydrocarbon group optionally having one or two or more substituents selected from a nitro group, an ether group, a carbonyl group, an ester group and an amide group.

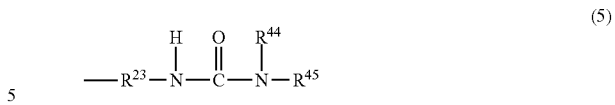
(5)

where $R^{23}$ represents a $C_{1-20}$ divalent hydrocarbon group, and each of $R^{44}$ and $R^{45}$ independently represent a hydrogen atom or a $C_{1-30}$ hydrocarbon group optionally having one or two or more substituents selected from a nitro group, an ether group, a carbonyl group, an ester group and an amide group. However, $R^{44}$ and $R^{45}$ may not both be hydrogen atoms.

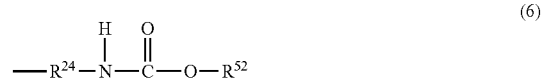
(6)

where $R^{24}$ represents a $C_{1-20}$ divalent hydrocarbon group, and $R^{52}$ represents a $C_{1-30}$ hydrocarbon group optionally having one or two or more substituents selected from a nitro group, an ether group, a carbonyl group, an ester group and an amide group.

G in General Formula (I) represents a group represented by General Formula (1), J represents a group represented by General Formula (2), $X^1$ represents a group represented by General Formula (3) or a group represented by General Formula (4) and $X^2$ represents a group represented by General Formula (5) or a group represented by General Formula (6), and these groups are explained in detail below. Each of g and j represent a number from 1 to 10,000. In General Formula (I) above, G and J are represented as being in a block sequence, but the sequence of G and J may be either block or random, or a combination of block and random parts. A sequence that is a mixture of block parts and random parts is preferred because it makes it easy to obtain the effects of the present invention.

$R^{21}$ in General Formula (1) represents a $C_{1-20}$ divalent hydrocarbon group, and examples include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, linear undecylene, branched undecylene, linear dodecylene, branched dodecylene, linear tridecylene, branched tridecylene, linear tetradecylene, branched tetradecylene, linear pentadecylene, branched pentadecylene, linear hexadecylene, branched hexadecylene, linear heptadecylene, branched heptadecylene, linear octadecylene, branched octadecylene, linear nonadecylene, branched nonadecylene, linear icosylene, branched icosylene, cyclopentylene and cyclohexylene groups; and aromatic hydrocarbon groups such as phenylene, methylphenylene, ethylphenylene, propylphenylene, butylphenylene, dimethylphenylene, diethylphenylene, dipropylphenylene, dibutylphenylene, trimethylphenylene, triethylphenylene, tripropylphenylene, tributylphenylene, tetramethylphenylene, tetraethylphenylene, tetrapropylphenylene, xylylene and phenethylene groups. Of these, an aliphatic hydrocarbon group is preferred for obtaining a greater thickening and gelling effect on silicone oils and ester oils, a $C_{1-10}$ aliphatic hydrocarbon group is more preferred, and a $C_6$ aliphatic hydrocarbon group is still more preferred. A group derived from the diisocyanate compound represented by General Formula (B) (which is a starting material of the polyurethane polyurea of the present invention), or in other words a group in which the two isocyanate groups are removed from this diisocyanate compound, is preferred for ease of manufacture.

Each of $R^1$ and $R^{10}$ in General Formula (1) independently represent a $C_{1-4}$ divalent hydrocarbon group, and examples of such groups include a methylene group; an ethylene group; a propane-1,3-diyl (linear propylene) group; branched propylene groups such as propane-1,2-diyl and propane-2,2-diyl; linear butylene groups such as butane-1,4-diyl, butane-1,2-diyl, butane-1,3-diyl, butane-2,3-diyl, butane-1,1-diyl and butane-2,2-diyl; and branched butylene groups such as 2-methylpropane-1,3-diyl and 2-methylpropane-1,2-diyl. Of these, an ethylene, propane-1,3-diyl, propane-1,2-diyl or propane-2,2-diyl group is preferred, and an ethylene group is more preferred for increasing the thickening and gelling effect of the polyurethane polyurea of the present invention. All of the $R^1$ groups may be the same, or they may be different groups. Similarly, all of the $R^{10}$ groups may be the same, or they may be different groups.

$R^2$ and $R^9$ in General Formula (1) represent $C_{1-10}$ divalent hydrocarbon groups, and examples of such groups include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, cyclopentylene and cyclohexylene groups; and aromatic hydrocarbon groups such as phenylene, methylphenylene, ethylphenylene, propylphenylene, butylphenylene, dimethylphenylene, diethylphenylene and phenethylene groups. Of these, a divalent aliphatic hydrocarbon group is preferred for increasing the thickening and gelling effect of the polyurethane polyurea of the present invention, an ethylene, linear propylene or branched propylene group is more preferred, an ethylene or linear propylene group is still more preferred, and a linear propylene group is especially preferred.

Each of m and p independently represent a number from 0 to 10, and to increase the thickening and gelling effects of the polyurethane polyurea of the present invention, m is preferably 1 to 4, or more preferably 1 or 2, or most preferably 1. The average value of n represents a number from 0 to 2,000, and to increase the thickening and gelling effects of the polyurethane polyurea of the present invention, it is preferably 10 to 1,000, or more preferably 20 to 500, or still more preferably 30 to 200, or yet more preferably 35 to 135, or most preferably 35 to 65.

Each of $R^3$ to $R^8$ in General Formula (1) independently represent a $C_{1-10}$ hydrocarbon group, a group represented by General Formula (1-1) or a group represented by General Formula (1-2), and of these, a $C_{1-10}$ hydrocarbon group is preferred because the starting material is easy to obtain. All of the $R^5$ groups in General Formula (1) may be the same, or they may be different groups. Similarly, all of the $R^6$ groups in General Formula (1) may be the same, or they may be different groups. Examples of the $C_{1-10}$ hydrocarbon group include aliphatic hydrocarbon groups such as methyl, ethyl, linear propyl, branched propyl, linear butyl, branched butyl, linear pentyl, branched pentyl, linear hexyl, branched hexyl, linear heptyl, branched heptyl, linear octyl, branched octyl, linear nonyl, branched nonyl, linear decyl, branched decyl, cyclopentyl and cyclohexyl groups; and aromatic hydrocarbon groups such as phenyl, methylphenyl, ethylphenyl, propylphenyl, butylphenyl, dimethylphenyl, diethylphenyl and phenethyl groups. Of these, a methyl, ethyl, linear propyl or branched propyl group is preferred for ease of obtaining the starting materials, a methyl or ethyl group is more preferred, and a methyl group is still more preferred.

$R^{11}$ in General Formula (1-1) represents a $C_{1-10}$ divalent hydrocarbon group, and examples of such groups include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, cyclopentylene and cyclohexylene groups; and aromatic hydrocarbon groups such as phenylene, methylphenylene, ethylphenylene, propylphenylene, butylphenylene, dimethylphenylene, diethylphenylene and phenethylene groups. Of these, a divalent aliphatic hydrocarbon group is preferred for increasing the thickening and gelling effects of the polyurethane polyurea of the present invention, an ethylene, linear propylene or branched propylene group is more preferred, and an ethylene or linear propylene group is still more preferred.

$R^{12}$ in General Formula (1-1) represents a $C_{1-4}$ divalent hydrocarbon group, and examples of such groups include a methylene group; an ethylene group; a propane-1,3-diyl (linear propylene) group; branched propylene groups such as propane-1,2-diyl and propane-2,2-diyl; linear butylene groups such as butane-1,4-diyl, butane-1,2-diyl, butane-1,3-diyl, butane-2,3-diyl, butane-1,1-diyl and butane-2,2-diyl; and branched butylene groups such as 2-methylpropane-1,3-diyl and 2-methylpropane-1,2-diyl. Of these, an ethylene, propane-1,3-diyl, propane-1,2-diyl or propane-2,2-diyl group is preferred for increasing the thickening and gelling effects of the polyurethane polyurea of the present invention, and an ethylene group is especially desirable. All of the $R^{12}$ groups may be the same group, or they may be different groups. q represents a number from 0 to 10, and q is preferably 1 to 4 or more preferably 1 or 2 in order to increase the thickening and gelling effects of the polyurethane polyurea of the present invention.

In General Formula (1-2), $R^{11}$ represents a $C_{1-10}$ divalent hydrocarbon group, $R^{12}$ represents a $C_{1-4}$ divalent hydrocarbon group and q represents a number from 0 to 10, and the $R^{11}$, $R^{12}$ and q here are not explained in detail because they are equivalent to the $R^{11}$, $R^{12}$ and q in General Formula (1-1) as explained above. Moreover, in General Formula (1-2) G' represents a group represented by General Formula (1), J' represents a group represented by General Formula (2) and $X^3$ represents a group represented by General Formula (5) or a group represented by General Formula (6), and these are likewise not explained in detail because they are equivalent to the G, J and $X^2$ in General Formula (I). Each of e and f independently represents a number from 0 to 10,000, and although G' and J' are represented as being in a block sequence in General Formula (1-2), the sequence of G' and J' may be either block or random, or a combination of block and random parts.

$R^{22}$ in General Formula (2) represents a $C_{1-20}$ divalent hydrocarbon group, and examples include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, linear undecylene, branched undecylene, linear dodecylene, branched dodecylene, linear tridecylene, branched tridecylene, linear tetradecylene, branched tetradecylene, linear pentadecylene, branched pentadecylene, linear hexadecylene, branched hexadecylene, linear heptadecylene, branched heptadecylene, linear octadecylene, branched octadecylene, linear nonadecylene, branched nonadecylene, linear icosylene, branched icosylene, cyclopentylene and cyclohexylene groups; and aromatic hydrocarbon groups such as phenylene, methylphenylene, ethylphenylene, propylphenylene, butylphenylene, dimethylphenylene, diethylphenylene, dipropylphenylene, dibutylphenylene, trimethylphenylene, triethylphenylene, tripropylphenylene, tributylphenylene, tetramethylphenylene, tetraethylphenylene, tetrapropylphenylene, xylylene and phenethylene groups. Of these, an aliphatic hydrocarbon group is preferred for obtaining a greater thickening and gelling effect on silicone oils and ester oils, a $C_{1-10}$ aliphatic hydrocarbon group is more preferred, and a $C_6$ aliphatic hydrocarbon group is still more preferred. A group derived from the diisocyanate compound represented by General Formula (B) (which is a starting material of the polyurethane polyurea of the present invention), or in other words a group in which the two isocyanate groups are removed from this diisocyanate compound, is preferred for ease of manufacture.

$R^{30}$ in General Formula (2) represents a $C_{1-10}$ divalent hydrocarbon group, and examples of such groups include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, cyclopentylene and cyclohexylene groups; and aromatic hydrocarbon groups such as phenylene, methylphenylene, ethylphenylene, propylphenylene, butylphenylene, dimethylphenylene, diethylphenylene and phenethylene groups. Of these, a $C_{1-6}$ divalent aliphatic hydrocarbon group is preferred because the starting material is easy to obtain, an ethylene, linear butylene, linear pentylene or linear hexylene group is more preferred, and an ethylene group is still more preferred. t represents the number 0 or 1.

Each of $R^{42}$ and $R^{43}$ in General Formula (3) independently represent a hydrogen atom or a $C_{1-30}$ hydrocarbon group optionally having one or two or more substituents selected from a nitro group, an ether group, a carbonyl group, an ester group and an amide group. However, $R^{42}$ and $R^{43}$ may not both be hydrogen atoms. When the $C_{1-30}$ hydrocarbon group does not have a substituent, it may be, for example, an alkyl group such as a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, eicosyl, henicosyl, heneicosyl, docosyl, tricosyl, tetracosyl, pentacosyl, hexacosyl, heptacosyl, octacosyl, nonacosyl or triacontyl group (these groups may be linear or branched, and may be secondary or tertiary); an alkenyl group such as a vinyl, allyl, propenyl, butenyl, pentenyl, hexenyl, heptenyl or octenyl group (these groups may be linear or branched, and may be secondary or tertiary); an aryl group such as a phenyl, toluyl, xylyl, cumenyl, mesityl, benzyl, phenethyl, styryl, cinnamyl, benzhydryl, trityl, ethylphenyl, propylphenyl, butylphenyl, pentylphenyl, hexylphenyl, heptylphenyl, octylphenyl, nonylphenyl, decylphenyl, undecylphenyl, dodecylphenyl, styrenated phenyl, p-cumylphenyl, phenylphenyl, benzylphenyl, α-naphthyl or β-naphthyl group; or a cycloalkyl group such as a cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl or methylcycloheptenyl group. When the $C_{1-30}$ hydrocarbon group has a substituent, it may have either a substituent selected from a nitro group, an ether group, a carbonyl group, an ester group and an amide group substituted for a hydrogen atom at one or two or more positions on the hydrocarbon group, or else one or two or more carbon atoms of the hydrocarbon group may be substituted to introduce the substituent(s) into one or two or more positions in the hydrocarbon group, as long as the group has a total of 1 to 30 carbon atoms. Of these, a group derived from the nitrogen compound represented by General Formula (D) (which is a starting material of the polyurethane polyurea of the present invention), or in other words a group corresponding to that nitrogen compound, is preferred because the starting material is easy to obtain. To obtain good reactivity and increase the thickening and gelling effect of the resulting polyurethane polyurea of the present invention, preferably either one of $R^{42}$ and $R^{43}$ is a hydrogen atom while the other is a $C_{1-20}$ hydrocarbon group, or more preferably either one of $R^{42}$ and $R^{43}$ is a hydrogen atom while the other is a $C_{1-10}$ hydrocarbon group, or still more preferably either one of $R^{42}$ and $R^{43}$ is a hydrogen atom while the other is a $C_{2-6}$ hydrocarbon group. When either or both of $R^{42}$ and $R^{43}$ are a hydrocarbon group, the hydrocarbon preferably has no substituent because this makes it easier to control the reaction when preparing the polyurethane polyurea of the present invention.

$R^{51}$ in General Formula (4) represents a $C_{1-30}$ hydrocarbon group optionally having one or two or more substituents selected from a nitro group, an ether group, a carbonyl group, an ester group and an amide group. When the $C_{1-30}$ hydrocarbon group does not have a substituent, it may be, for example, an alkyl group such as a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, eicosyl, henicosyl, heneicosyl, docosyl, tricosyl, tetracosyl, pentacosyl, hexacosyl, heptacosyl, octacosyl, nonacosyl or triacontyl group (these groups may be linear or branched, and may be secondary or tertiary); an alkenyl group such as a vinyl, allyl, propenyl, butenyl, pentenyl, hexenyl, heptenyl or octenyl group (these groups may be linear or branched, and may be secondary or tertiary); an aryl group such as a phenyl, toluyl, xylyl, cumenyl, mesityl, benzyl, phenethyl, styryl, cinnamyl, benzhydryl, trityl, ethylphenyl, propylphenyl, butylphenyl, pentylphenyl, hexylphenyl, heptylphenyl, octylphenyl, nonylphenyl, decylphenyl, undecylphenyl, dodecylphenyl, styrenated phenyl, p-cumylphenyl, phenylphenyl, benzylphenyl, α-naphthyl or β-naphthyl group; or a cycloalkyl group such as a cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl or methylcycloheptenyl group. When the $C_{1-30}$ hydrocarbon group has a substituent, it may have either a substituent selected from a nitro group, an ether group, a carbonyl group, an ester group and an amide group substituted for a hydrogen atom at one or two or more positions on the hydrocarbon group, or else one or two or more carbon atoms of the hydrocarbon group may be substituted to introduce the substituent(s) into one or two or more positions in the hydrocarbon group, as long as the group has a total of 1 to 30 carbon atoms. Of these, a group derived from the hydroxyl group-containing compound represented by General Formula (E) (which is a starting material of the polyurethane polyurea of the present invention), or in other words a group corresponding to that hydroxyl group-containing compound, is preferred because the starting material is easy to obtain. To obtain good reactivity and increase the thickening and gelling effects of the resulting polyurethane polyurea of the present invention, a $C_{1-20}$ hydrocarbon group is preferred, a $C_{1-10}$ hydrocarbon group is more preferred, and a $C_{2-8}$ hydrocarbon group is still more preferred. In $R^{51}$, the hydrocarbon preferably has no substituent because this makes it easier to control the reaction when preparing the polyurethane polyurea of the present invention.

$R^{23}$ in General Formula (5) represents a $C_{1-20}$ divalent hydrocarbon, and examples include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, linear undecylene, branched undecylene, linear dodecylene, branched dodecylene, linear tridecylene, branched tridecylene, linear tetradecylene, branched tetradecylene, linear pentadecylene, branched pentadecylene, linear hexadecylene, branched hexadecylene, linear heptadecylene, branched heptadecylene, linear octadecylene, branched octadecylene, linear nonadecylene, branched nonadecylene, linear icosylene, branched icosylene, cyclopentylene and cyclohexylene groups; and aromatic hydrocarbon groups such as phenylene, methylphenylene, ethylphenylene, propylphenylene, butylphenylene, dimethylphenylene, diethylphenylene, dipropylphenylene, dibutylphenylene, trimethylphenylene, triethylphenylene, tripropylphenylene, tributylphenylene, tetramethylphenylene, tetraethylphenylene, tetrapropylphenylene, xylylene and phenethylene groups. Of these, an aliphatic hydrocarbon group is preferred for obtaining a greater thickening and gelling effect on silicone oils and ester oils, a $C_{1-10}$ aliphatic hydrocarbon group is more preferred, and a $C_6$ aliphatic hydrocarbon group is still more preferred. A group derived from the diisocyanate compound represented by General Formula (B) (which is a starting material of the polyurethane polyurea of the present invention), or in other words a group in which the two isocyanate groups are removed from this diisocyanate compound, is preferred for ease of manufacture.

Each of $R^{44}$ and $R^{45}$ in General Formula (5) independently represent a hydrogen atom or a $C_{1-30}$ hydrocarbon group optionally having one or two or more substituents selected from a nitro group, an ether group, a carbonyl group, an ester group and an amide group. However, $R^{44}$ and $R^{45}$ may not both be hydrogen atoms. When the $C_{1-30}$ hydrocarbon group does not have a substituent, it may be, for example, an alkyl group such as a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, eicosyl, henicosyl, heneicosyl, docosyl, tricosyl, tetracosyl, pentacosyl, hexacosyl, heptacosyl, octacosyl, nonacosyl or triacontyl group (these groups may be linear or branched, and may be secondary or tertiary); an alkenyl group such as a vinyl, allyl, propenyl, butenyl, pentenyl, hexenyl, heptenyl or octenyl group (these groups may be linear or branched, and may be secondary or tertiary); an aryl group such as a phenyl, toluyl, xylyl, cumenyl, mesityl, benzyl, phenethyl, styryl, cinnamyl, benzhydryl, trityl, ethylphenyl, propylphenyl, butylphenyl, pentylphenyl, hexylphenyl, heptylphenyl, octylphenyl, nonylphenyl, decylphenyl, undecylphenyl, dodecylphenyl, styrenated phenyl, p-cumylphenyl, phenylphenyl, benzylphenyl, α-naphthyl or β-naphthyl group; or a cycloalkyl group such as a cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl or methylcycloheptenyl group. When the $C_{1-30}$ hydrocarbon group has a substituent, it may have either a substituent selected from a nitro group, an ether group, a carbonyl group, an ester group and an amide group substituted for a hydrogen atom at one or two or more positions on the hydrocarbon group, or else one or two or more carbon atoms of the hydrocarbon group may be substituted to introduce the substituent(s) into one or two or more positions in the hydrocarbon group, as long as the group has a total of 1 to 30 carbon atoms. Of these, a group derived from the nitrogen compound represented by General Formula (D) (which is a starting material of the polyurethane polyurea of the present invention), or in other words a group corresponding to that nitrogen compound, is preferred because the starting material is easy to obtain. To obtain good reactivity and increase the thickening and gelling effects of the resulting polyurethane polyurea of the present invention, preferably either one of $R^{44}$ and $R^{45}$ is a hydrogen atom while the other is a $C_{1-20}$ hydrocarbon group, or more preferably either one of $R^{44}$ and $R^{45}$ are a hydrogen atom while the other is a $C_{1-10}$ hydrocarbon group, or still more preferably either one of $R^{44}$ and $R^{45}$ is a hydrogen atom while the other is a $C_{2-6}$ hydrocarbon group in the nitrogen compound. When either or both of $R^{44}$ and $R^{45}$ is a hydrocarbon group, the hydrocarbon preferably has no substituent because this makes it easier to control the reaction when preparing the polyurethane polyurea of the present invention.

$R^{24}$ in General Formula (6) represents a $C_{1-20}$ divalent hydrocarbon group, and examples include aliphatic hydrocarbon groups such as methylene, ethylene, linear propylene, branched propylene, linear butylene, branched butylene, linear pentylene, branched pentylene, linear hexylene, branched hexylene, linear heptylene, branched heptylene, linear octylene, branched octylene, linear nonylene, branched nonylene, linear decylene, branched decylene, linear undecylene, branched undecylene, linear dodecylene, branched dodecylene, linear tridecylene, branched tridecylene, linear tetradecylene, branched tetradecylene, linear pentadecylene, branched pentadecylene, linear hexadecylene, branched hexadecylene, linear heptadecylene, branched heptadecylene, linear octadecylene, branched octadecylene, linear nonadecylene, branched nonadecylene, linear icosylene, branched icosylene, cyclopentylene and cyclohexylene groups; and aromatic hydrocarbon groups such as phenylene, methylphenylene, ethylphenylene, propylphenylene, butylphenylene, dimethylphenylene, diethylphenylene, dipropylphenylene, dibutylphenylene, trimethylphenylene, triethylphenylene, tripropylphenylene, tributylphenylene, tetramethylphenylene, tetraethylphenylene, tetrapropylphenylene, xylylene and phenethylene groups. Of these, an aliphatic hydrocarbon group is preferred for obtaining strong thickening and gelling effects on silicone oils and ester oils, a $C_{1-10}$ aliphatic hydrocarbon group is more preferred, and a $C_6$ aliphatic hydrocarbon group is still more preferred. A group derived from the diisocyanate compound represented by General Formula (B) (which is a starting material of the polyurethane polyurea of the present invention), or in other words a group in which the two isocyanate groups are removed from this diisocyanate compound, is preferred for ease of manufacture.

$R^{52}$ in General Formula (6) represents a $C_{1-30}$ hydrocarbon group optionally having one or two or more substituents selected from a nitro group, an ether group, a carbonyl group, an ester group and an amide group. When the $C_{1-30}$ hydrocarbon group does not have a substituent, it may be, for example, an alkyl group such as a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, eicosyl, henicosyl, heneicosyl, docosyl, tricosyl, tetracosyl, pentacosyl, hexacosyl, heptacosyl, octacosyl, nonacosyl or triacontyl group (these groups may be linear or branched, and may be secondary or tertiary); an alkenyl group such as a vinyl, allyl, propenyl, butenyl, pentenyl, hexenyl, heptenyl or octenyl group (these groups may be linear or branched, and may be secondary or tertiary); an aryl group such as a phenyl, toluyl, xylyl, cumenyl, mesityl, benzyl, phenethyl, styryl, cinnamyl, benzhydryl, trityl, ethylphenyl, propylphenyl, butylphenyl, pentylphenyl, hexylphenyl, heptylphenyl, octylphenyl, nonylphenyl, decylphenyl, undecylphenyl, dodecylphenyl, styrenated phenyl, p-cumylphenyl, phenylphenyl, benzylphenyl, α-naphthyl or β-naphthyl group; or a cycloalkyl group such as a cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl or methylcycloheptenyl group. When the $C_{1-30}$ hydrocarbon group has a substituent, it may have either a substituent selected from a nitro group, an ether group, a carbonyl group, an ester group and an amide group substituted for a hydrogen atom at one or two or more positions on the hydrocarbon group, or else one or two or more carbon atoms of the hydrocarbon group may be substituted to introduce the substituent(s) into one or two or more positions in the hydrocarbon group, as long as the group has a total of 1 to 30 carbon atoms. Of these, a group derived from the hydroxyl group-containing compound represented by General Formula (E) (which is a starting material of the polyurethane polyurea of the present invention), or in other words a group corresponding to that hydroxyl group-containing compound, is preferred because the starting material is easy to obtain. To obtain good reactivity and increase the thickening and gelling effects of the resulting polyurethane polyurea of the present invention, a $C_{1-20}$ hydrocarbon group is preferred, a $C_{1-10}$ hydrocarbon group is more preferred, and a $C_{2-8}$ hydrocarbon group is still more preferred. In $R^{52}$, the hydrocarbon preferably has no substituent because this makes it easier to control the reaction when preparing the polyurethane polyurea of the present invention.

The inventors have previously disclosed (Japanese Patent Application Publication No. 2011-225729) that a polymer similar to the polyurethane polyurea of the present invention and having siloxane bonds and urethane bonds in the molecule can yield an elastic, gel-like composition when added to silicone oil or ester oil. However, the polyurethane polyurea of the present invention differs from that of the previous invention in being a novel polymer having urea bonds in the molecule in addition to siloxane bonds and urethane bonds, and having at least one or more urea bonds in the main chain rather than at the ends of the polyurethane polyurea, and this difference is a condition of the polyurethane polyurea exhibiting the effects of the present invention. In this Description, "main chain" signifies the "-$(G)_q$-$(J)_j$-" part in General Formula (I), or in other words the structure of the polyurethane polyurea represented by General Formula (I) in which $X^1$ and $X^2$ are removed (and $X^3$ in General Formula (1-2) is removed when any of $R^3$ to $R^8$ in General Formula (1) is a group represented by General Formula (1-2)). "Ends" here means the "—$X^1$" and "—$X^2$" parts in General Formula (I), and indicates the structure of the polyurethane polyurea represented by General Formula (I) in which the "-$(G)_q$-$(J)_j$-" part (including $X^3$ in General Formula (1-2) when any of $R^3$ to $R^8$ in General Formula (1) is a group represented by General Formula (1-2)) is removed. Even if the polyurethane polyurea of the present invention has urea bonds in the main chain, the effects of the present invention are not obtained if the main chain does not contain urethane bonds, or in other words if the main chain contains only urea bonds, so both a urethane bond and at least one or more urea bonds must be present in the main chain. When a urea bond is present in the main chain in addition to a urethane bond, because the urea bond has a stronger hydrogen binding force than the urethane bond, the polyurethane polyurea molecules associate with each other when added to silicone oils or ester oils, which can greatly increase the thickening and gelling effects. That is, in comparison with the polymer described in Japanese Patent Application Publication No. 2011-225729 above, the polyurethane polyurea of the present invention is capable of thickening and gelling a greater variety of silicone oils and ester oils, and these silicone oils and ester oils can be thickened and gelled with a smaller added amount of the polyurethane polyurea. This also helps to stabilize the polymer molecule because urea bonds are harder to hydrolyze than urethane bonds.

To more easily obtain the effects of the present invention, the ratio of the numbers of urethane bonds and urea bonds in the main chain is preferably 4:1 to 100:1 (urethane bonds:urea bonds), or more preferably 5:1 to 80:1, or still more preferably 5:1 to 50:1, or yet more preferably 5:1 to 20:1. The numbers of urethane bonds and urea bonds in the polyurethane polyurea of the present invention as a whole differ depending on which of the groups represented by General Formulae (3) to (6) are located at the ends of the polyurethane polyurea, and the numbers of urethane bonds and urea bonds in the polyurethane polyurea as a whole are determined by the amounts of each of the groups represented by General Formulae (3) to (6). Irrespective of these, however, from the standpoint of obtaining the effects of the present invention it is desirable that the ratio of the numbers of urethane bonds and urea bonds in the main chain (the structure represented by General Formula (I) in which $X^1$ and $X^2$ are removed) be 4:1 to 100:1.

The fact that the ratio of the numbers of urethane bonds and urea bonds in the main chain of the polyurethane polyurea of the present invention is preferably 4:1 to 100:1 (urethane bonds:urea bonds) can be explained as follows. For example, if none of $R^3$ to $R^8$ in the group represented by General Formula (1) (G in the polyurethane polyurea represented by General Formula (I)) is a group represented by General Formula (1-2), and t in the group represented by General Formula (2) (J in the polyurethane polyurea represented by General Formula (I)) is 0, the relationship between g and j in General Formula (I) is preferably 2g:j=4:1 to 100:1, while if none of $R^3$ to $R^8$ in the group represented by General Formula (1) (G in the polyurethane polyurea represented by General Formula (I)) is a group represented by General Formula (1-2), and t in the group represented by General Formula (2) (J in the polyurethane polyurea represented by General Formula (I)) is 1, the relationship between g and j in General Formula (I) is preferably 2g:2j=4:1 to 100:1. On the other hand, if either one of $R^3$ and $R^4$ in the group represented by General Formula (1) (G in the polyurethane polyurea represented by General Formula (I)) is a group represented by General Formula (1-2) and t in the group represented by General Formula (2) (J in the polyurethane polyurea represented by General Formula (I)) is 0, the relationship between g and j in General Formula (I) and e and f in General Formula (1-2) is preferably (2g+2e+1):(j+f)=4:1 to 100:1, while if either one of $R^3$ and $R^4$ in the group represented by General Formula (1) (G in the polyurethane polyurea represented by General Formula (I)) is a group represented by General Formula (1-2) and t in the group represented by General Formula (2) (J in the polyurethane polyurea represented by General Formula (I)) is 1, the relationship between g and j in General Formula (I) and e and f in General Formula (1-2) is preferably (2g+2e+1):(2j+2f)=4:1 to 100:1. Cases in which 2 or more of $R^3$ to $R^8$ in the group represented by General Formula (1) (G in the polyurethane polyurea represented by General Formula (I)) are groups represented by General Formula (1-2) can be considered in the same way, and relationship expressions can be derived.

The method for manufacturing the polyurethane polyurea of the present invention represented by General Formula (I) is not specified, and it may be manufactured by a known method, but from the standpoint of ease of manufacture and availability of the starting materials, it is preferably manufactured by reacting a polyurethane polyurea prepolymer obtained from a silicone derivative starting material made up of one or two or more compounds represented by General Formula (A), a diisocyanate compound starting material made up of one or two or more compounds represented by General Formula (B) and a starting material made up of one or two or more compounds represented by General Formula (C) with either or both of a nitrogen compound made up of one or two or more compounds represented by General Formula (D) and a hydroxyl group-containing compound made up of one or two or more compounds represented by General Formula (E).

Examples of silicone oils that can be thickened and gelled by the polyurethane polyurea of the present invention include dimethylpolysiloxane, methyl phenyl polysiloxane, decamethyl tetracyclosiloxane, octamethyl trisiloxane, alkyl-modified dimethylpolysiloxane, polyether-modified dimethylpolysiloxane, silicone resin, fatty acid-modified polysiloxane, higher alcohol-modified polysiloxane and amino-modified polysiloxane. Of these, dimethylpolysiloxane and cyclic dimethylpolysiloxane are the most widely used and are preferred for maximizing the thickening and gelling effects. The molecular weights and viscosities of these silicone oils are not limited, but because silicone oils with large molecular weights are highly viscous they may not require gelling, or may be difficult to use because they become too hard when gelled. Therefore, the kinematic viscosity of the silicone oil at 25° C. is preferably 1 to 500 mm²/s, or more preferably 1 to 100 mm²/s, or still more preferably 1 to 50 mm²/s, or yet more preferably 1 to 10 mm²/s.

The amount of the polyurethane polyurea of the present invention that is added to the silicone oil is not particularly specified, but preferably 0.1 to 20.0 parts by mass or more preferably 0.5 to 15.0 parts by mass or still more preferably 1.5 to 10.0 parts by mass of the polyurethane polyurea of the present invention is added per 100 parts by mass of the silicone oil. If the added amount of the polyurethane polyurea is less than 0.1 parts by mass per 100 parts by mass of the silicone oil, the gelling effects may not be obtained, while if it exceeds 20.0 parts by mass the effects may not be commensurate with the added amount, or the polyurethane polyurea may not dissolve completely in the silicone oil. When adding the polyurethane polyurea of the present invention to silicone oil to manufacture a silicone oil composition, the polyurethane polyurea of the present invention can simply be added to the silicone oil and mixed to obtain a uniform mixture. The temperature during mixing is not particularly limited, and for example the mixture can be heated to from room temperature to about 200° C., and mixed until uniform.

An ester oil that can be thickened and gelled by the polyurethane polyurea of the present invention may be any ester group-containing compound having one or more ester bonds in the molecule and a molecular weight of 120 or more. Specific examples include synthetic ester oils such as hexyl acetate, decyl acetate, butyl propionate, hydrogenated polybutene myristyl myristate, hexyl laurate, decyl oleate, branched propyl myristate, hexyldecyl dimethyl octanoate, glycerin monostearate, diethyl phthalate, ethylene glycol monostearate and octyl oxystearate; and triglycerides (triester oils) such as lanolin, mink oil, cacao butter, coconut oil, palm seed oil, camellia oil, sesame seed oil, castor oil and olive oil. However, the gelling effects are not obtained by mixing the gelling agent of the present invention with an ester oil with a molecular weight of less than 120, such as ethyl acetate or butyl acetate.

The amount of the polyurethane polyurea of the present invention that is added to the ester oil is not particularly specified, but preferably 0.1 to 20.0 parts by mass, or more preferably 0.5 to 15.0 parts by mass, or still more preferably 1.5 to 10.0 parts by mass of the polyurethane polyurea of the present invention is added per 100 parts by mass of the ester oil. If the added amount of the polyurethane polyurea per 100 parts by mass of the ester oil is less than 0.1 parts by mass the gelling effects may not be obtained, while if it exceeds 20.0 parts by mass the effects may not be commensurate with the added amount, or the polyurethane polyurea may not dissolve completely in the ester oil. When adding the polyurethane polyurea of the present invention to an ester oil to manufacture an ester oil composition, the polyurethane polyurea of the present invention can simply be added to the ester oil and mixed to obtain a uniform mixture. The temperature during mixing is not particularly limited, and for example the mixture can be heated from room temperature to about 200° C., and mixed until uniform. The gelling effects are also obtained if the polyurethane polyurea of the present invention is added to an oil obtained by previously mixing a silicone oil and an ester oil.

When the polyurethane polyurea of the present invention is used as a gelling agent, the applications thereof are not limited, and it can be used for any application for which silicone oil or ester oil is used. Examples include fields such as lubricants, cosmetics, medicines, perfumes, coatings, and fibers, but it is preferably used in cosmetics, for which the consistency of the gelled composition and the feel of the gelled composition when touched are important considerations for the final product. When a silicone oil or ester oil that has been thickened or gelled with the polyurethane polyurea of the present invention is used in a cosmetic composition, it is stable as an oily component and easy to apply and spread on the skin, and therefore contributes to improving the functionality and range of uses of the cosmetic composition. A silicone oil composition and an ester oil composition that have been thickened and gelled by the polyurethane polyurea of the present invention can also be mixed and used together as necessary.

Applications such as the following are possible when the polyurethane polyurea of the present invention is used other than as a gelling agent. The polyurethane polyurea of the present invention is a novel polymer having urea bonds in the molecule in addition to siloxane bonds and urethane bonds, and having at least one or more urea bonds in the main chain rather than at the ends of the polyurethane polyurea. When a polymer has siloxane bonds and urethane bonds, it can be used in applications such as heat-resistant oils, flame-retardant oils and novel solvents for cosmetics because these bonds are highly heat resistant. Moreover, because urea bonds have an even stronger hydrogen bonding force than siloxane bonds and urethane bonds, and are thus more resistant to hydrolysis, the polyurethane polyurea of the present invention is a polymer that is not only heat resistant but also highly water resistant, corrosion resistant and chemical resistant, and can be alternatively used in various applications where such properties are required.

The cosmetic composition of the present invention is a cosmetic composition containing a silicone oil composition and/or ester oil composition that has been thickened and gelled by the polyurethane polyurea of the present invention. In terms of specific products, examples of the cosmetic composition include sunscreens containing various UV inhibitors, foundations, W/O emulsions (skin milk), creams, cleansing oils, hair waxes, hair creams and perfumes. Moreover, other additives commonly used in cosmetic compositions can be used to confer various properties as appropriate when manufacturing these cosmetic compositions, within a qualitative and quantitative range that does not detract from the effects of the present invention. Examples of such additives include powder components, liquid oils and fats, solid oils and fats, waxes, hydrocarbon oils, higher fatty acids, higher alcohols, anionic surfactants, cationic surfactants, amphoteric surfactants, non-ionic surfactants, humectants, polymer compounds, sequestrants, lower alcohols, polyhydric alcohols, sugars, amino acids and their derivatives, organic amines, pH adjusters, antioxidants, preservatives, blood circulation promoters, anti-inflammatories, activators, whiteners, antiseborrheic agents, anti-inflammatory agents, and various extracts and plant and seaweed extracts, and one or two or more of these may be optionally compounded.

Examples of the powder components include inorganic powders (such as talc, kaolin, mica, silk mica (sericite), muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium, silica, zeolite, barium sulfate, calcined calcium sulfate (baked gypsum), calcium phosphate, fluorapatite, hydroxyapatite, ceramic powders, metal soaps (for example, zinc myristate, calcium palmitate, aluminum stearate), and boron nitride); organic powders (such as polyamide resin powder (nylon powder), polyethylene powder, polymethyl methacrylate powder, polystyrene powder, styrene-acrylic acid copolymer resin powder, benzoguanamine resin powder, polytetrafluoroethylene powder and cellulose powder); inorganic white pigments (such as titanium dioxide and zinc oxide); inorganic red pigments (such as iron oxide (red ochre) and iron titanate); inorganic brown pigments (such as γ-iron oxide); inorganic yellow pigments (such as yellow iron oxide and loess); inorganic black pigments (such as black iron oxide and low-order titanium oxide); inorganic violet pigments (such as manganese violet and cobalt violet); inorganic green pigments (such as chromium oxide, chromium hydroxide and cobalt titanate); inorganic blue pigments (such as ultramarine and Prussian blue); pearl pigments (such as titanium oxide coated mica, titanium oxide coated bismuth oxychloride, titanium oxide coated talc, colored titanium oxide coated mica, bismuth oxychloride and argentine); metal powder pigments (such as aluminum powder and copper powder); organic pigments such as zirconium, barium and aluminum lakes (for example, organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404; and Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1); and natural dyes (such as chlorophyll and β-carotene).

Examples of the liquid oils and fats include avocado oil, camellia oil, turtle oil, macadamia nut oil, corn oil, mink oil, olive oil, canola oil, egg-yolk oil, sesame seed oil, persic oil, wheat germ oil, sasanqua oil, castor oil, linseed oil, safflower oil, cottonseed oil, perilla oil, soybean oil, peanut oil, tea oil, kaya oil, rice bran oil, paulownia oil, Japanese tung oil, jojoba oil, germ oil and triglycerine.

Examples of the solid oils and fats include cocoa butter, coconut oil, hardened coconut oil, palm oil, palm kernel oil, *Rhus succedanea* kernel oil, hardened oil, *Rhus succedanea* and hardened castor oil.

Examples of the waxes include beeswax, candelilla wax, cottonseed wax, carnauba wax, bayberry wax, Chinese wax, spermaceti, montan wax, rice bran wax, lanolin, kapok wax, lanolin acetate, liquid lanolin, sugarcane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of the hydrocarbon oils include fluid paraffin, ozocerite, squalane, pristane, paraffin, ceresin, squalene, vaseline, and microcrystalline wax.

Examples of the higher fatty acids include lauric acid, myristic acid, palmitic acid, stearic acid, behenic acid, oleic acid, undecylenic acid, tall oil fatty acids, isostearic acid, linoleic acid, linolenic acid, eicosapentaenoic acid (EPA) and docosahexaenoic acid (DHA).

Examples of the higher alcohols include linear alcohols (such as lauryl alcohol, cetyl alcohol, stearyl alcohol, behenyl alcohol, myristyl alcohol, oleyl alcohol and cetostearyl alcohol); and branched alcohols (such as monostearyl glycerin ether (batyl alcohol), 2-decyltetradecanol, lanolin alcohol, cholesterol, phytosterol, hexyldodecanol, isostearyl alcohol and octyldodecanol).

Examples of the anionic surfactants include fatty acid soaps (such as sodium laurate and sodium palmitate); higher alkyl sulfate ester salts (such as sodium lauryl sulfate and potassium lauryl sulfate); alkyl ether sulfate ester salts (such as POE-lauryl sulfate triethanolamine and POE-sodium lauryl sulfate); N-acyl sarcosinic acids (such as sodium lauroyl sarcosinate); higher fatty acid amide sulfonic acid salts (such as N-myristoyl-N-methyltaurine sodium, coconut oil fatty acid methyltaurine sodium and lauryl methyltaurine sodium); phosphoric acid ester salts (such as POE-oleyl ether sodium phosphate and POE-stearyl ether phosphate); sulfosuccinic acid salts (such as sodium di-2-ethylhexyl sulfosuccinate, monolauroyl monoethanolamide sodium polyoxyethylene sulfosuccinate and lauryl polypropylene glycol sodium sulfosuccinate); alkylbenzene sulfonic acid salts (such as sodium linear dodecylbenzene sulfonate, linear dodecylbenzene sulfonate triethanolamine and linear dodecylbenzene sulfonic acid); higher fatty acid ester sulfuric acid ester salts (such as hardened coconut oil fatty acid glycerin sodium sulfate); N-acyl glutamic acid salts (such as N-lauroyl monosodium glutamate, N-stearoyl disodium glutamate and N-myristoyl-L-monosodium glutamate); sulfated oils (such as Turkey red oil); POE-alkyl ether carboxylic acids; POE-alkyl allyl ether carboxylic acid salts; α-olefin sulfonic acid salts; higher fatty acid sulfate ester salts; secondary alcohol sulfuric acid ester salts; higher fatty acid alkylolamide sulfuric acid ester salts; sodium lauroyl monoethanolamide succinate; ditriethanolamine N-palmitoyl aspartate; and sodium casein.

Examples of the cationic surfactants include alkyl trimethyl ammonium salts (such as stearyl trimethyl ammonium chloride and lauryl trimethyl ammonium chloride); alkyl pyridinium salts (such as cetyl pyridinium chloride); distearyl dimethyl ammonium chloride dialkyl dimethyl ammonium salt; polychlorides (N,N'-dimethyl-3,5-methylene piperidinium); alkyl quaternary ammonium salts; alkyl dimethylbenzyl ammonium salts; alkyl isoquinolinium salts; dialkyl morpholinium salts; POE-alkylamines; alkylamine salts; polyamine fatty acid derivatives; amyl alcohol fatty acid derivatives; benzalkonium chloride; and benzethonium chloride.

Examples of the amphoteric surfactants include imidazoline amphoteric surfactants (such as 2-undecyl-N,N,N-(hydroxyethylcarboxymethyl)-2-imidazoline sodium, and 2-cocoyl-imidazolinium hydroxide-1-carboxyethyloxy disodium salt); and betaine surfactants (such as 2-heptadecyl-N-carboxymethyl-N-hydroxyethyl imidazolinium betaine, lauryl dimethylaminoacetic acid betaine, alkyl betaine, amidobetaine and sulfobetaine).

Examples of the non-ionic surfactants include sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate); glycerin polyglycerin fatty acids (such as mono-cottonseed oil fatty acid glycerin, glycerin monoerucate, glycerin sesquioleate, glycerin monostearate, glycerin α,α'-oleate pyroglutamate and glycerin monostearate malate); propylene glycol fatty acid esters (such as propylene glycol monostearate); hardened castor oil derivatives; glycerin alkyl ethers; POE-sorbitan fatty acid esters (such as POE-sorbitan monooleate, POE-sorbitan monostearate, POE-sorbitan monooleate and POE-sorbitan tetraoleate); POE-sorbitol fatty acid esters (such as POE-sorbitol monolaurate, POE-sorbitol monooleate, POE-sorbitol pentaoleate and POE-sorbitol monostearate); POE-glycerin fatty acid esters (such as POE-glycerin monostearate, POE-glycerin monoisostearate, POE-glycerin triisostearate and POE-monooleates); POE-fatty acid esters (such as POE-distearate, POE-monodioleate and ethylene glycol distearate); POE-alkyl ethers (such as POE-lauryl ether, POE-oleyl ether, POE-stearyl ether, POE-behenyl ether, POE-2-octyldodecyl ether and POE-cholestanol ether); pluronic type compounds (such as Pluronic); POE.POP alkyl ethers (such as POE-POP-cetyl ether, POE.POP-2-decyl tetradecyl ether, POE.POP-monobutyl ether, POE.POP-hydrogenated lanolin and POE.POP-glycerin ether); tetra-POE.tetra-POP ethylenediamine condensates (such as Tetronic); POE-castor oil and hardened castor oil derivatives (such as POE-castor oil, POE-hardened castor oil, POE-hardened castor oil monoisostearate, POE-hardened castor oil triisostearate, POE-hardened castor oil monopyroglutamate monoisostearate diester and POE-hardened castor oil maleate); POE-beeswax lanolin derivatives (such as POE-sorbitol beeswax); alkanolamides (such as coconut oil fatty acid diethanolamide, lauric acid monoethanolamide and fatty acid isopropanolamide); POE-propylene glycol fatty acid esters; POE-alkylamines; POE-fatty acid amides; sucrose fatty acid esters; alkylethoxydimethylamine oxide; and trioleyl phosphoric acid.

Examples of the humectants include polyethylene glycol, xylitol, sorbitol, maltitol, chondroitin sulfate, hyaluronic acid, mucoitin sulfate, charonic acid, atelocollagen, cholesteryl-12-hydroxystearate, sodium lactate, bile acid salts, DL-pyrrolidone carboxylic acid salt, short-chain soluble collagen, diglycerin (EO) PO adduct, *Rosa roxburghii* extract, *Achillea millefolium* extract and melilot extract.

Examples of the natural water-soluble polymers include plant-based polymers (such as gum arabic, tragacanth gum, galactan, guar gum, carob gum, karaya gum, carrageenan, pectin, agar, quince seed, algecolloid (brown algae extract), starch (rice, corn, potato, wheat) and glycyrrhizic acid); microbial polymers (such as xanthan gum, dextran, succinoglucan, pullulan and gellan gum); and animal polymers (such as collagen, casein, albumin and gelatin).

Examples of the water-soluble polymers include starch polymers (such as carboxymethyl starch and methyl hydroxypropyl starch); cellulose polymers (such as methyl cellulose, ethyl cellulose, methyl hydroxypropyl cellulose, hydroxyethyl cellulose, sodium cellulose sulfate, hydroxypropyl cellulose, carboxymethyl cellulose, sodium carboxymethyl cellulose, crystal cellulose and cellulose powder); alginic acid polymers (such as sodium alginate and alginic acid propylene glycol ester); vinyl polymers (such as polyvinyl alcohol, polyvinyl methyl ether, polyvinylpyrrolidone and carboxyvinyl polymer); polyoxyethylene polymers (such as polyoxyethylene-polyoxypropylene copolymers of polyethylene glycol 20,000, 40,000 and 60,000); acrylic polymers (such as sodium polyacrylate, polyethylene acrylate and polyacrylamide); polyethylenimine; and cationic polymers.

Examples of the sequestrants include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and ethylenediamine hydroxyethyl triacetic acid trisodium salt.

Examples of the lower alcohols include ethanol, propanol, isopropanol, isobutyl alcohol and t-butyl alcohol.

Examples of the polyhydric alcohols include trihydric alcohols (such as glycerin and trimethylol propane); tetrahydric alcohols (such as pentaerythritol); pentahydric alcohols (such as xylitol); hexahydric alcohols (such as sorbitol and mannitol); polyhydric alcohol polymers (such as diethylene glycol, dipropylene glycol, triethylene glycol, polypropylene glycol, tetraethylene glycol, diglycerin, polyethylene glycol, triglycerin, tetraglycerin and polyglycerin); dihydric alcohol alkyl ethers (such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibutyl ether); dihydric alcohol alkyl ethers (such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether); dihydric alcohol ether esters (such as ethylene glycol monomethyl ether acetate, ethylene glycol monoethyl ether acetate, ethylene glycol monobutyl ether acetate, ethylene glycol monophenyl ether acetate, ethylene glycol dilapidate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate); glycerin monoalkyl ethers (such as chimyl alcohol, selachyl alcohol and batyl alcohol); sugar alcohols (such as sorbitol, maltitol, maltotriose, mannitol, sucrose, erythritose, glucose, fructose, starch-degraded sugars, maltose, xylitose and reduction alcohols of starch-degraded sugars); Glysolid; tetrahydrofurfuryl alcohol; POE-tetrahydrofurfuryl alcohol; POP-butyl ether; POP.POE-butyl ether; tripolyoxypropylene glycerin ether; POP-glycerin ether; POP-glycerin ether phosphoric acid; POP.POE-pentaerythritol ether; and polyglycerin.

Examples of the monosaccharides include trioses (such as D-glyceryl aldehyde and dihydroxyacetone); tetroses (such as D-erythrose, D-erythrulose, D-threose and erythritose); pentoses (such as L-arabinose, D-xylose, L-lyxose, D-arabinose, D-ribose, D-ribulose, D-xylulose and L-xylulose); hexoses (such as D-glucose, D-talose, D-psicose, D-galactose, D-fructose, L-galactose, L-mannose and D-tagatose); heptoses (such as aldoheptose and heplose); octoses (such as octulose); deoxy sugars (such as 2-deoxy-D-ribose, 6-deoxy-L-galactose and 6-deoxy-L-mannose); amino sugars (such as D-glucosamine, D-galactosamine, sialic acid, aminouronic acid and muramic acid); uronic acids (such as D-glucuronic acid, D-mannuronic acid, L-gluronic acid, D-galacturonic acid and L-iduronic acid).

Examples of the oligosaccharides include sucrose, umbelliferose, lactose, planteose, isolychnoses, α,α-trehalose, raffinose, lychnoses, umbilicin, stachyose and verbascose.

Examples of the polysaccharides include cellulose, quince seed, chondroitin sulfate, starch, galactan, dermatan sulfate, glycogen, gum arabic, heparan sulfate, hyaluronic acid, gum tragacanth, keratan sulfate, chondroitin, xanthan gum, mucoitin sulfate, guar gum, dextran, keratosulfate, locust bean gum, succinoglucan and charonic acid.

Examples of the amino acids include neutral amino acids (such as threonine and cysteine) and basic amino acids (such as hydroxylysine). Examples of the amino acid derivatives include sodium acyl sarcosine (sodium lauroyl sarcosine), acyl glutamic acid salt, sodium acyl β-alanine, glutathione and pyrrolidone carboxylic acid.

Examples of the organic amines include monoethanolamine, diethanolamine, triethanolamine, morpholine, triisopropanolamine, 2-amino-2-methyl-1,3-propanediol, and 2-amino-2-methyl-1-propanol.

Examples of the pH adjusters include buffers such as lactic acid-sodium lactate, citric acid-sodium citrate and succinic acid-sodium succinate.

Examples of the vitamins include vitamins A, B1, B2, B6, C and E and their derivatives, pantothenic acid and its derivatives, and biotin.

Examples of the antioxidants include tocopherols, dibutyl hydroxytoluene, butyl hydroxyanisole, and gallic acid esters.

Other compatible ingredients include, for example, preservatives (such as methylparaben, ethylparaben, butylparaben and phenoxyethanol); anti-inflammatories (such as glycyrrhizic acid derivatives, glycyrrhetinic acid derivatives, salicylic acid derivatives, hinokitiol, zinc oxide and allantoin); whiteners (such as Saxifraga sarmentosa extract and arbutin); various extracts (such as Phellodendron amurense, Coptis japonica, Lithospermum root, Paeonia lactiflora, Swertia japonica, birch, sage, Eriobotrya japonica, carrot, aloe, mallow, iris, grape, coix seed, sponge gourd, lily, saffron, cnidium rhizome, ginger, Hypericum erectum, Ononis spinosa, garlic, red pepper, dried tangerine peel, Angelica acutiloba and seaweed); activators (such as royal jelly, photosensitizers and cholesterol derivatives); blood circulation promoters (such as nicotinic acid benzyl ester, nicotinic acid β-butoxyethyl ester, capsaicin, zingerone, cantharides tincture, ichthammol, tannic acid, α-borneol, nicotinic acid tocopherol, inositol hexanicotinate, cyclandelate, cinnarizine, tolazoline, acetylcholine, verapamil, cepharanthine, and γ-oryzanol); antiseborrheic agents (such as sulfur and thianthol); and anti-inflammatory agents (such as tranexamic acid, thiotaurine and hypotaurine).

EXAMPLES

The present invention is explained in detail below using examples, but the present invention is not limited by these examples, and changes may be made to the extent that these do not deviate from the scope of the present invention. Unless otherwise specified, % values in the examples below and the like are based on mass.

The starting materials used in manufacturing the polyurethane polyurea are shown below. The weight-average molecular weight of the silicone derivative represented by General Formula (A) is a value calculated using the number of hydroxyl groups in the silicone derivative and the hydroxyl value of the silicone derivative as measured based on JIS K 0070 (1992).

Silicone Derivative Represented by General Formula A

Silicone Derivative 1

A compound with a weight-average molecular weight of 3,000 in which $R^1$ and $R^{10}$ in General Formula (A) are ethylene groups, $R^2$ and $R^9$ are linear propylene groups, $R^4$ to $R^8$ are methyl groups, m and p are both 1 and the average of n=36.

Silicone Derivative 2

A compound with a weight-average molecular weight of 5,000 in which $R^1$ and $R^{10}$ in General Formula (A) are ethylene groups, $R^2$ and $R^9$ are linear propylene groups, $R^4$ to $R^8$ are methyl groups, m and p are both 1 and the average of n=63.

Silicone Derivative 3

A compound with a weight-average molecular weight of 7,000 in which $R^1$ and $R^{10}$ in General Formula (A) are ethylene groups, $R^2$ and $R^9$ are linear propylene groups, $R^4$ to $R^8$ are methyl groups, m and p are both 1 and the average of n=90.

Silicone Derivative 4

A compound with a weight-average molecular weight of 10,000 in which $R^1$ and $R^{10}$ in General Formula (A) are ethylene groups, $R^2$ and $R^9$ are linear propylene groups, $R^4$ to $R^8$ are methyl groups, m and p are both 1 and the average of n=131.

(Diisocyanate Compound Represented by General Formula (B))

Diisocyanate Compound 1

Hexamethylene diisocyanate (HDI) ($R^{20}$ in General Formula (B)=n-hexylene group)

Compound Represented by General Formula (C)

Compound 1

Ethylenediamine (in General Formula (C), $R^{30}$=ethylene group, y=1)

Compound 2
 Water (in General Formula (C), $R^{30}$=oxygen atom, y=0)
Nitrogen Compound Represented by General Formula (D)
 Nitrogen Compound 1
  Diethylamine ($R^{40}$ and $R^{41}$ in General Formula (D)=ethyl groups)
 Nitrogen Compound 2
  Aniline ($R^{40}$=hydrogen atom, $R^{41}$=phenyl group in General Formula (D))
Hydroxyl Group-Containing Compound Represented by General Formula (E)
 Hydroxyl Group-Containing Compound 1
  Ethanol ($R^{50}$ in General Formula (E)=ethyl group)
 Hydroxyl Group-Containing Compound 2
  n-octanol ($R^{50}$ in General Formula (E)=octyl group)
 Hydroxyl Group-Containing Compound 3
  2-ethyhexanol ($R^{50}$ in General Formula (E)=2-ethylhexyl group)
 Hydroxyl Group-Containing Compound 4
  Phenol ($R^{50}$ in General Formula (E)=phenyl group)

The methods for manufacturing the polymers used in the examples and comparative examples are as follows.

Compound of Example: Manufacture of Polymer 1

300 g (0.1 moles) of the Silicone Derivative 1, 0.84 g (0.014 moles) of ethylenediamine (Compound 1), 1,200 g of butyl acetate as a solvent and 0.46 g of dibutyl tin bis(2-ethylhexylthiogluconate) as a catalyst were loaded into a 4-necked flask with a capacity of 3,000 ml equipped with a thermometer, a nitrogen introduction pipe and a stirrer, the inside of the system was purged with nitrogen and the temperature was raised to 75° C., after which 24.9 g (0.148 moles) of hexamethylene diisocyanate (Diisocyanate Compound 1) were added and reacted for 2 hours at 70° C. to 80° C. After completion of the reaction, 3.1 g (0.068 moles) of ethanol (Hydroxyl group-containing Compound 1) were added and reacted for 3 hours at 70° C. to 80° C., and the reaction was terminated after the absence of isocyanate absorption had been verified with an infrared (IR) spectrometer (meaning that all the isocyanate had been reacted). The butyl acetate solvent was removed from the resulting reaction product with an evaporator to obtain a Polymer 1.

Compounds of Examples: Manufacture of Polymers 2 to 17

Polymers 2 to 17 were obtained by reacting the various starting materials by the same manufacturing methods used for Polymer 1, in the compounded amounts shown in Table 1. The solvents and catalysts using during manufacture of Polymers 2 to 17 were the same as those used during manufacture of Polymer 1, and in the same quantities. The numerical values in Table 1 represent the molar amounts of the starting materials used when manufacturing each polymer.

TABLE 1

| Polymer material | Example 1 Polymer 1 | Example 2 Polymer 2 | Example 3 Polymer 3 | Example 4 Polymer 4 | Example 5 Polymer 5 | Example 6 Polymer 6 | Example 7 Polymer 7 | Example 8 Polymer 8 | Example 9 Polymer 9 |
|---|---|---|---|---|---|---|---|---|---|
| Silicone derivative 1 | 0.1 | | | | 0.1 | | | | 0.1 |
| Silicone derivative 2 | | 0.1 | | | | 0.1 | | | |
| Silicone derivative 3 | | | 0.1 | | | | 0.1 | | |
| Silicone derivative 4 | | | | 0.1 | | | | 0.1 | |
| Diisocyanate compound 1 | 0.148 | 0.148 | 0.148 | 0.148 | 0.148 | 0.148 | 0.148 | 0.148 | 0.148 |
| Compound 1 | 0.014 | 0.014 | 0.014 | 0.014 | | | | | |
| Compound 2 | | | | | 0.028 | 0.028 | 0.028 | 0.028 | 0.028 |
| Nitrogen compound 1 | | | | | | | | | |
| Nitrogen compound 2 | | | | | | | | | |
| OH-containing compound 1 | 0.068 | 0.068 | 0.068 | 0.068 | 0.04 | 0.04 | 0.04 | 0.04 | |
| OH-containing compound 2 | | | | | | | | | 0.04 |
| OH-containing compound 3 | | | | | | | | | |
| OH-containing compound 4 | | | | | | | | | |
| Ratio of urethane bonds and urea bonds in main chain (urethane bonds:urea bonds) | 7:1 | 7:1 | 7:1 | 7:1 | 7:1 | 7:1 | 7:1 | 7:1 | 7:1 |

| Polymer material | Example 10 Polymer 10 | Example 11 Polymer 11 | Example 12 Polymer 12 | Example 13 Polymer 13 | Example 14 Polymer 14 | Example 15 Polymer 15 | Example 16 Polymer 16 | Example 17 Polymer 17 |
|---|---|---|---|---|---|---|---|---|
| Silicone derivative 1 | 0.1 | 0.1 | 0.1 | 0.1 | 0.1 | 0.1 | 0.1 | 0.1 |
| Silicone derivative 2 | | | | | | | | |
| Silicone derivative 3 | | | | | | | | |
| Silicone derivative 4 | | | | | | | | |
| Diisocyanate compound 1 | 0.148 | 0.148 | 0.148 | 0.148 | 0.148 | 0.148 | 0.148 | 0.148 |
| Compound 1 | | | | | | | | |
| Compound 2 | 0.028 | 0.028 | 0.028 | 0.028 | 0.04 | 0.01 | 0.0033 | 0.0025 |
| Nitrogen compound 1 | | | | 0.04 | | | | |
| Nitrogen compound 2 | | | | | 0.04 | | | |
| OH-containing compound 1 | | | | | | 0.016 | 0.076 | 0.089 | 0.091 |
| OH-containing compound 2 | | | | | | | | |
| OH-containing compound 3 | 0.04 | | | | | | | |
| OH-containing compound 4 | | 0.04 | | | | | | |
| Ratio of urethane bonds and urea bonds in main chain (urethane bonds:urea bonds) | 7:1 | 7:1 | 7:1 | 7:1 | 5:1 | 20:1 | 60:1 | 80:1 |

Compound of Comparative Example: Manufacture of Polymer 18

300 g (0.1 moles) of the Silicone Derivative 1, 1,200 g of butyl acetate as a solvent, and 0.46 g of dibutyl tin bis(2-ethylhexylthiogluconate) as a catalyst were loaded into a 4-necked flask with a capacity of 3,000 ml equipped with a thermometer, a nitrogen introduction pipe and a stirrer, the inside of the system was purged with nitrogen and the temperature was raised to 75° C., after which 24.9 g (0.148 moles) of hexamethylene diisocyanate (Diisocyanate Compound 1) were added and reacted for 2 hours at 70° C. to 80° C. After completion of the reaction, 4.4 g (0.096 moles) of ethanol (Hydroxyl group-containing Compound 1) were added and reacted for 3 hours at 70° C. to 80° C., and the reaction was terminated after the absence of isocyanate absorption was verified with an infrared (IR) spectrometer (meaning that all the isocyanate had been reacted). The butyl acetate solvent was removed from the resulting reaction product with an evaporator to obtain a Polymer 18.

Compounds of Comparative Examples: Manufacture of Polymers 19 to 24

Polymers 19 to 24 were obtained by reacting the various starting materials by the same manufacturing methods used for Polymer 18, in the compounded amounts shown in Table 2. The solvents and catalysts using during manufacture of Polymers 19 to 24 were the same as those used during manufacture of Polymer 18, and in the same quantities. The numerical values in Table 2 represent the molar amounts of the starting materials used when manufacturing each polymer.

TABLE 2

| Polymer material | Comp Ex 1 Polymer 18 | Comp Ex 2 Polymer 19 | Comp Ex 3 Polymer 20 | Comp Ex 4 Polymer 21 | Comp Ex 5 Polymer 22 | Comp Ex 6 Polymer 23 | Comp Ex 7 Polymer 24 |
|---|---|---|---|---|---|---|---|
| Silicone derivative 1 | 0.1 | | | | 0.1 | 0.1 | 0.1 |
| Silicone derivative 2 | | 0.1 | | | | | |
| Silicone derivative 3 | | | 0.1 | | | | |
| Silicone derivative 4 | | | | 0.1 | | | |
| Diisocyanate compound 1 | 0.148 | 0.148 | 0.148 | 0.148 | 0.148 | 0.148 | 0.148 |
| Compound 1 | | | | | | | |
| Compound 2 | | | | | | | |
| Nitrogen compound 1 | | | | | | 0.096 | |
| Nitrogen compound 2 | | | | | | | 0.096 |
| OH-containing compound 1 | 0.096 | 0.096 | 0.096 | 0.096 | | | |
| OH-containing compound 2 | | | | | | | |
| OH-containing compound 3 | | | | | 0.096 | | |
| OH-containing compound 4 | | | | | | | |
| Ratio of urethane bonds and urea bonds in main chain (urethane bonds:urea bonds) | 100:0 | 100:0 | 100:0 | 100:0 | 100:0 | 100:0 | 100:0 |

Compounds of Comparative Examples: Other Thickening and Gelling Agents

The following compounds, which are commonly used as thickening and gelling agents, were used as comparative examples.

Comparative Example 8: 12-hydroxystearic acid
Comparative Example 9: Magnesium stearate
Comparative Example 10: Dextrin palmitate Thickening and Gelling Test Polymers 1 to 24 (of which Polymers 1 to 17 are examples and Polymers 18 to 24 are comparative examples) and the compounds of comparative examples 7 to 9 were added to the following two kinds of oil in amounts of 2.0 mass % to 10.0 mass %, heated at 80° C. to 90° C. and then stirred for one hour to homogenize the mixtures. 50 ml of each of the resulting solutions was added to a 100 ml glass bottle and left standing for 24 hours in a 25° C. thermostatic tank, and the condition of the oil after still standing and the external appearance were observed and evaluated according to the following standard. The results are shown in Table 3.

(Oils Used)

Oil 1: Cyclic silicone (viscosity 4 mm$^2$/S (25° C.))
Oil 2: Branched propyl myristate Standard for Judging Oil State ⊚: Jelly-like or gum-like
○: Gel-like viscous fluid
Δ: viscous fluid (viscous thickened oil)
∇: unhomogeneous fluid (gels or solid materials floating in the fluid.)
■: wax-like inelastic solid
▲: grease-like
▼: low-viscosity fluid (a viscosity does not visually change)
X: a thickening and gelling agent does not solve

TABLE 3

| | Oil 1 | | | | | Oil 2 | | | | |
|---|---|---|---|---|---|---|---|---|---|---|
| | Addition amount 2.0 mass % | Addition amount 3.0 mass % | Addition amount 5.0 mass % | Addition amount 7.5 mass % | Addition amount 10.0 mass % | Addition amount 2.0 mass % | Addition amount 3.0 mass % | Addition amount 5.0 mass % | Addition amount 7.5 mass % | Addition amount 10.0 mass % |
| Example 1 | ○ | ○ | ◉ | ◉ | ◉ | ○ | ○ | ◉ | ◉ | ◉ |
| Example 2 | ○ | ○ | ◉ | ◉ | ◉ | ○ | ○ | ◉ | ◉ | ◉ |
| Example 3 | Δ | Δ | ○ | ○ | ◉ | Δ | Δ | ○ | ○ | ◉ |
| Example 4 | Δ | Δ | ○ | ○ | ◉ | Δ | Δ | ○ | ○ | ◉ |
| Example 5 | ○ | ○ | ◉ | ◉ | ◉ | ○ | ○ | ◉ | ◉ | ◉ |
| Example 6 | ○ | ○ | ◉ | ◉ | ◉ | ○ | ○ | ◉ | ◉ | ◉ |
| Example 7 | Δ | Δ | ○ | ○ | ◉ | Δ | Δ | ○ | ○ | ◉ |
| Example 8 | Δ | Δ | ○ | ○ | ◉ | Δ | Δ | ○ | ○ | ◉ |
| Example 9 | ○ | ○ | ◉ | ◉ | ◉ | ○ | ○ | ◉ | ◉ | ◉ |
| Example 10 | ○ | ○ | ◉ | ◉ | ◉ | ○ | ○ | ◉ | ◉ | ◉ |
| Example 11 | ○ | ○ | ◉ | ◉ | ◉ | ○ | ○ | ◉ | ◉ | ◉ |
| Example 12 | ○ | ○ | ◉ | ◉ | ◉ | ○ | ○ | ◉ | ◉ | ◉ |
| Example 13 | ○ | ○ | ◉ | ◉ | ◉ | ○ | ○ | ◉ | ◉ | ◉ |
| Example 14 | ○ | ○ | ◉ | ◉ | ◉ | ○ | ○ | ◉ | ◉ | ◉ |
| Example 15 | ○ | ○ | ◉ | ◉ | ◉ | ○ | ○ | ◉ | ◉ | ◉ |
| Example 16 | Δ | Δ | ○ | ○ | ◉ | Δ | Δ | ○ | ○ | ◉ |
| Example 17 | Δ | Δ | ○ | ○ | ◉ | Δ | Δ | ○ | ○ | ◉ |
| Comp Ex 1 | ▼ | ▼ | ▼ | Δ | Δ | ▼ | ▼ | ▼ | Δ | Δ |
| Comp Ex 2 | ▼ | ▼ | ▼ | Δ | Δ | ▼ | ▼ | ▼ | Δ | Δ |
| Comp Ex 3 | ▼ | ▼ | ▼ | Δ | Δ | ▼ | ▼ | ▼ | Δ | Δ |
| Comp Ex 4 | ▼ | ▼ | ▼ | Δ | Δ | ▼ | ▼ | ▼ | Δ | Δ |
| Comp Ex 5 | ▼ | ▼ | ▼ | Δ | Δ | ▼ | ▼ | ▼ | Δ | Δ |
| Comp Ex 6 | ▼ | ▼ | ▼ | Δ | Δ | ▼ | ▼ | ▼ | ▼ | Δ |
| Comp Ex 7 | ▼ | ▼ | ▼ | Δ | Δ | ▼ | ▼ | ▼ | ▼ | Δ |
| Comp Ex 8 | ■ | ■ | ■ | ■ | ■ | ■ | ■ | ■ | ■ | ■ |
| Comp Ex 9 | ▼ | ▼ | ▼ | ▼ | ▼ | ▼ | ▼ | ▼ | ▼ | ▼ |
| Comp Ex 10 | X | X | X | X | X | X | ▼ | ▼ | ▼ | ▼ |

As a result, the Polymers 1 to 17, which are polyurethane polyureas of the present invention, exhibited thickening and gelling effects on both Oil 1 and Oil 2 even when added in small amounts.

INDUSTRIAL APPLICABILITY

The polyurethane polyurea of the present invention is a novel polymer capable of thickening and gelling silicone oils or ester oils into gel or jelly form even with a small added amount. The polyurethane polyurea of the present invention has greater heat resistance, water resistance, corrosion resistance and chemical resistance than conventional thickening and gelling agents, and is extremely useful because it may be used for various applications that were not available in the past.

The invention claimed is:

1. A polyurethane polyurea obtained by reacting a polyurethane polyurea prepolymer obtained from compounds consisting of a silicone derivative starting material made up of at least one compound of Formula (A) below, a diisocyanate compound starting material made up of at least one compound of Formula (B) below and a starting material made up of at least one compound of Formula (C) below, with a compound selected from the group consisting of a nitrogen compound made up of at least one compound of Formula (D) below, a hydroxyl group-containing compound made up of at least one compound of Formula (E) below, and combinations thereof:

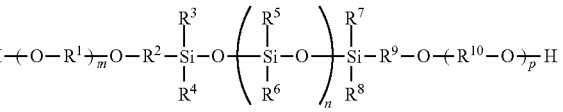
(A)

where $R^1$ and $R^{10}$ represent $C_{1-4}$ divalent hydrocarbon groups, $R^2$ and $R^9$ represent $C_{1-10}$ divalent hydrocarbon groups, each of $R^3$ to $R^8$ independently represent a $C_{1-10}$ hydrocarbon group or a group of Formula (a-1), each of m and p independently represent a number from 0 to 10, and the average value of n represents a number from 0 to 2,000;

(a-1)

where $R^{11}$ represents a $C_{1-10}$ divalent hydrocarbon group, $R^{12}$ represents a $C_{1-4}$ divalent hydrocarbon group, and q represents a number from 0 to 10;

OCN—$R^{20}$—NCO (B)

where $R^{20}$ represents a $C_{1-20}$ divalent hydrocarbon group;

(C)

where $R^{30}$ represents a $C_{1-10}$ divalent hydrocarbon group or oxygen atom, and y represents a number 0 or 1; however, when $R^{30}$ is a $C_{1-10}$ divalent hydrocarbon group, y represents the number 1, and when $R^{30}$ is an oxygen atom, y represents the number 0;

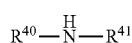 (D)

where each of $R^{40}$ and $R^{41}$ independently represent a hydrogen atom or a $C_{1-30}$ hydrocarbon group optionally having one or two or more substituents selected from the group consisting of a nitro group, an ether group, an ester group and an amide group; however, $R^{40}$ and $R^{41}$ may not both be hydrogen atoms;

 (E)

where $R^{50}$ represents a $C_{1-30}$ hydrocarbon group optionally having one or two or more substituents selected from the group consisting of a nitro group, an ether group, an ester group and an amide group, wherein the polyurethane polyurea is obtained by first manufacturing the polyurethane polyurea prepolymer using each starting material such that the amount of isocyanate groups in the diisocyanate compound starting material is 1.1 to 3.0 moles and the total amount of either or both of amino groups and water, when $R^{30}$ is oxygen, in the at least one compound of Formula (C) is 0.01 to 1.0 moles per mole of hydroxyl groups in the silicone derivative starting material, and then reacting the polyurethane polyurea prepolymer with the compound selected from the group consisting of the nitrogen compound, the hydroxyl-group containing compound, and combinations thereof such that the total amount of either or both of amino groups in the nitrogen compound and hydroxyl groups in the hydroxyl group-containing compound is 0.05 to 4.0 moles per mole of the hydroxyl groups in the silicone derivative starting material.

2. A silicone oil composition containing 0.1 to 20 parts by mass of the polyurethane polyurea according to claim 1 per 100 parts by mass of a silicone oil.

3. A cosmetic composition containing the silicone oil composition according to claim 2.

4. An ester oil composition containing 0.1 to 20 parts by mass of the polyurethane polyurea according to claim 1 per 100 parts by mass of an ester oil.

5. A cosmetic composition containing the ester oil composition according to claim 4.

* * * * *